(12) United States Patent
Wiemer

(10) Patent No.: US 9,745,331 B2
(45) Date of Patent: Aug. 29, 2017

(54) THERAPEUTIC BISPHOSPHONATES

(71) Applicant: UNIVERSITY OF IOWA RESEARCH FOUNDATION, Iowa City, IA (US)

(72) Inventor: David Wiemer, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 0 days.

(21) Appl. No.: 14/412,578

(22) PCT Filed: Jul. 3, 2013

(86) PCT No.: PCT/US2013/049341
§ 371 (c)(1),
(2) Date: Jan. 2, 2015

(87) PCT Pub. No.: WO2014/008407
PCT Pub. Date: Jan. 9, 2014

(65) Prior Publication Data
US 2015/0322099 A1    Nov. 12, 2015

Related U.S. Application Data

(60) Provisional application No. 61/668,299, filed on Jul. 5, 2012.

(51) Int. Cl.
| C07F 9/38 | (2006.01) |
| A61K 31/663 | (2006.01) |
| C07F 9/653 | (2006.01) |
| C07F 9/6506 | (2006.01) |

(52) U.S. Cl.
CPC .......... *C07F 9/3839* (2013.01); *A61K 31/663* (2013.01); *C07F 9/3826* (2013.01); *C07F 9/3847* (2013.01); *C07F 9/3856* (2013.01); *C07F 9/3882* (2013.01); *C07F 9/653* (2013.01); *C07F 9/65062* (2013.01)

(58) Field of Classification Search
CPC ............................ A61K 31/663; C07F 9/3847
See application file for complete search history.

(56) References Cited

U.S. PATENT DOCUMENTS

| 4,383,052 A | 5/1983 | Higo |
| 4,559,157 A | 12/1985 | Smith |
| 4,608,392 A | 8/1986 | Jacquet |
| 4,732,998 A * | 3/1988 | Binderup ................ C07F 9/386 |
| | | 558/161 |
| 4,774,262 A | 9/1988 | Blanquet et al. |
| 4,820,508 A | 4/1989 | Wortzman |
| 4,938,949 A | 7/1990 | Borch et al. |
| 4,992,478 A | 2/1991 | Geria |
| 5,583,122 A | 12/1996 | Benedict et al. |
| 6,727,234 B2 | 4/2004 | Wiemer et al. |
| 7,268,124 B2 | 9/2007 | Wiemer et al. |

| 2004/0167102 A1 | 8/2004 | Wiemer et al. |
| 2006/0079487 A1 | 4/2006 | Sanders |
| 2008/0200679 A1 | 8/2008 | McKenna |

FOREIGN PATENT DOCUMENTS

| WO | 9719091 A1 | 5/1997 |
| WO | 2008/28056 A1 | 10/2008 |

OTHER PUBLICATIONS

Szabo et al. (J. Med. Chem. 2002, 45, 2185-2196).*
Kubinyi (3D QSAR in Drug Design: Ligand-Protein Interactions and Molecular Similarity, vol. 2-3, Springer, 1998, 800 pages). pp. 243-44 provided.*
Wermuth, The Practice of Medicinal Chemsitry, 2d ed. (2003), 768 pages. Chs. 9-10 provided.*
Wiemer et al. (Bioorg. Med. Chem. 16 (2008) 3652-3660).*
Ebetino et al. (Bone 49 (2011) 20-33).*
Armstrong, et al., "cDNA cloning and expression of the alpha and beta subunits of rat Rab geranylgeranyl transferase.", J. Biol. Chem. 268: 12221-12229 (1993).
Benford, et al., "Farnesol and geranylgeraniol prevent activation of caspases by aminobisphosphonates: biochemical evidence for two distinct pharmacological classes of bisphosphonate drugs", Mol Pharmacol. 56 (1):131-140 (1999).
Bergstrom, et al., "Alendronate is a specific, nanomolar inhibitor of farnesyl diphosphate synthase", Arch Biochem Biophys. 373(1):231-241 (2000).
Cohen, et al., "Inhibition of human smooth muscle cell proliferation in culture by farnesyl pyrophosphate analogues, inhibitors of in vitro protein: Farnesyl transferase", Biochemical Pharmacology, vol. 57, No. 4, 365-474, 1999.

(Continued)

Primary Examiner — Robert Havlin
(74) Attorney, Agent, or Firm — Viksnins Harris Padys Malen LLP

(57) ABSTRACT

The invention provides novel pyrophosphate synthase inhibitors of formula I and formula II as well salts thereof; the invention also provides compositions comprising such inhibitors and methods for their use.

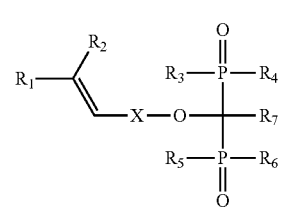

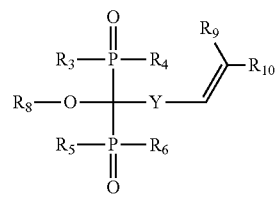

4 Claims, 7 Drawing Sheets

(56) References Cited

OTHER PUBLICATIONS

Ebetino, et al., "Recent Work on the Synthesis of Phosphonate-containing, Bone-active Heterocycles", Heterocycles 30:855-862 (1990).
Ericsson, et al., "Distribution of prenyltransferases in rat tissues", J. Biol. Chem. 268: 832-838 (1993).
Ericsson, et al., "Human geranylgeranyl diphosphate synthase: isolation of the cDNA, chromosomal mapping and tissue expression", J. Lipid Res. 39(9):1731-1739 (1998).
Fairlamb, et al., "Cycloisomerisation of modified terpenoid 1,6-enynes-synthesis of conformationally-restricted cyclic frarnesyl analogues", Tetrahedron Letters, vol. 43, No. 30, 5327-5331, 2002.
Fisher, et al., "Alendronate mechanism of action: geranylgeraniol, an intermediate in the mevalonate pathway, prevents inhibition of osteoclast formation, bone resorption, and kinase activation in vitro", PNAS, 96(1):133-138 (1999).
Fuse, et al., "Regulation of geranylgeranyl pyrophosphate synthase in the proliferation of rat FRTL-5 cells: involvement of both cAMP-PKA and PI3-AKT pathways", Biochem Biophys Res Commun. 315(4):1147-1153 (2004).
Holstein, et al., "Consequences of Mevalonate Depletion", J. Biol. Chem. 277:10678-10682 (2002).
Holstein, et al., "Isoprenoid pyrophosphate analogues regulate expression of Ras-related proteins", Biochemistry 42 (15):4384-4391 (2003).
Holstein, et al., "Isoprenoids influence expression of Ras and Ras-related proteins", Biochemistry 41:13698-13704 (2002).
Holstein, et al., "Phosphonate and bisphosphonate analogues of farnesyl pyrophosphate as potential inhibitors of farnesyl protein transferase", Bioorg Med Chem. 6(6):6876-94 (1998).
Hutchinson, et al., "Synthesis of alkylated methylene bisphosphonates via organothallium intermediates", Journal of Organometallic Chemistry, vol. 291, No. 2, 145-151, 1985.
Keller, et al., "Mechanism of aminobisphosphonate action: characterization of alendronate inhibition of the isoprenoid pathway", Biochem Biophys Res Commun. 266:560-563 (1999).
Luckman, et al., "Nitrogen-containing bisphosphonates inhibit the mevalonate pathway and prevent post-translational prenylation of GTP-binding proteins, including Ras", J. Bone Miner. Res. 13(4):581-589 (1998).
Martin, et al., "Bisphosphonates inhibit the growth of Trypanosoma brucei, Trypanosoma cruzi, Leishmania donovani, Toxoplasma gondii, and Plasmodium falciparum: A potential route to chemotherapy", J. Med. Chem. 44 (6):909-916 (2001).
McKenna, et al., "The facile dealkylation of phosphonic acid dialkyl esters by bromotrimethylsilane", Tetrahedron Lett. 18:155-158 (1977).
Moomaw, et al., "Mammalian protein geranylgeranyltransferase. Subunit composition and metal requirements", J. Biol. Chem. 267:17438-17443 (1992).
Muehlbauer, et al., "Effect of various polyphosphonates on ectopic calcification and bone resorption in rats", Mineral and Electrolyte Metabolism, vol. 5, No. 6, 296-303, 1981.
Patent Cooperation Treaty, International Searching Authority, Search Report and Written Opinion for PCT/US2013/049341, 10 pages, Sep. 4, 2013.
Quimby, et al., "Metalated methylenediphosphate esters. Preparation, characterisation and synthetic applications", Journal of Organometallic Chemistry, vol. 291, No. 2, 145-151, 1968.
Reilly, et al., "In vitro studies in a myelogenous leukemia cell line suggest an organized binding of geranylgeranyl diphosphate synthase inhibitors", Biochemical Pharmacology 96, 83-92 (2015).
Reiss, et al., "Inhibition of purified p21ras farnesyl:protein transferase by Cys-AAX tetrapeptides", Cell 62(1):81-8 (1990).
Reszka, et al., "Bisphosphonates Act Directly on the Osteoclast to Induce Caspase Cleavage of Mst1 Kinase during Apoptosis", J. Biol. Chem. 274:34967-34973 (1999).
Sagami, et al., "Studies on geranylgeranyl diphosphate synthase from rat liver: specific inhibition by 3-azageranylgeranyl diphosphate", Arch Biochem Biophys. 297(2):314-320 (1992).
Shull, et al., "Synthesis and biological activity of isoprenoid bisphosphonates", Bioorg Med Chem., 14(12), 4130-4136 (2006).
Spear, et al., "Molecular cloning and promoter analysis of the rat liver farnesyl diphosphate synthase gene", J. Biol. Chem. 267: 14462-14469 (1992).
Valentinjn, et al., "Synthesis of Pyrophosphonic Acid Analogues of Farnesyl Pyrophosphate", Tetrahedron, vol. 51, No. 7, 2099-2108, 1995.
Van Beek, et al., "Farnesyl pyrophosphate synthase is the molecular target of nitrogen-containing bisphosphonates", Biochem Biophys Res Commun. 264(1):108-111 (1999).
Van Beek, et al., "The role of geranylgeranylation in bone resorption and its suppression by bisphosphonates in fetal bone explants in vitro: A clue to the mechanism of action of nitrogen-containing bisphosphonates", J Bone Miner Res. 14(5):722-729 (1999).
Vepsalainen, et al., "Bisphosphonate prodrugs: a new synthetic strategy to tetraacyloxymethyl esters of methylenebisphosphonates", Tetrahedron. Lett. 40:8491-8493 (1999).
Vicent, et al., "The Branch Point Enzyme of the Mevalonate Pathway for Protein Prenylation Is Overexpressed in the bb/ob Mouse and Induced by Adipogenesis", Mol. Cellular Biol. 20:2158-2166 (2000).
Virtanen, et al., "Alendronate inhibits invasion of PC-3 prostate cancer cells by affecting the mevalonate pathway", Cancer Res. 62(9):2708-2714 (2002).
Xing, et al., "Lovastatin is antiarrhythmic in ischemic heart tissue by blocking triggered activity", J. of Invest. Med. 53 (2):S368 (2005).
Yokoyama, et al., "Purification of a mammalian protein geranylgeranyltransferase. Formation and catalytic properties of an enzyme-geranylgeranyl pyrophosphate complex", J Biol Chem. 268(6):4055-4060 (1993).
Zenitani, et al., "Gerfelin, a novel inhibitor of geranylgeranyl diphosphate synthase from Beauveria felina QN22047. I. Taxonomy, fermentation, isolation, and biological activities", J Antibiot (Tokyo). 56(7):617-621 (2003).
Zhou, et al., "Synthesis of isoprenoid bisphosphonate ethers through C—P bond formations: Potential inhibitors of geranylgeranyl diphosphate synthase", Beilstein J Org Chem 10, 1645-1650 (2014).
Gao, et al., "Discovery of potent inhibiotr for farnesyl pyrophosphate synthase in the mevalonate pathway", Chem Commun 46, 5340-5342 (2010).
Haelters, et al., "Synthesis of functionalized alkoxyalkylidene gem-bisphosphonates", Tetrahedron 64(27), 6537-6543 (2008).
Lecercle, et al., "A Facile Anchoring the Bisphosphonate Moiety into Alcohols and Phenols through Copper Carbenoid Mediated O—H Insertion Reaction", Synlett 12, 1863-1868 (2007).
Turhanen, et al., "Synthesis of Novel Fatty Acide Derivatives of Etidronic Acid", Synthesis 18, 3063-3066 (2005).
Wiemer, et al., "Digeranyl Bisphosphonate Inhibits Geranylgeranyl Pyrophosphate Synthase", Biochemical and Biophysical Research Communications, vol. 353, 921-925 (2007).

* cited by examiner

THERAPEUTIC BISPHOSPHONATES

PRIORITY OF INVENTION

This application claims priority to U.S. Provisional Application No. 61/668,299, filed Jul. 5, 2012. The entire content of this provisional application is incorporated herein by reference.

BACKGROUND

Farnesyl pyrophosphate (FPP) and geranylgeranyl pyrophosphate (GGPP) are branch-point intermediates in the isoprenoid biosynthetic pathway. These isoprenoids are synthesized via a series of sequential condensations of five-carbon units catalyzed by the enzymes FPP synthase and GGPP synthase, respectively. FPP sits at the branch-point between sterol and longer chain non-sterol synthesis. GGPP is a precursor for ubiquinone synthesis, and in plants it serves as the precursor for carotenoids, diterpenes, and chlorophylls. FPP and GGPP also serve as isoprene donors in the isoprenylation of proteins catalyzed by the enzymes farnesyl protein transferase (FPTase) and geranylgeranyl protein transferase (GGPTase) I and II. Isoprenylation of proteins, in particular small GTPases, serves to ensure proper intracellular localization and function.

While expression of FPP synthase has been shown to be regulated by sterol availability, GGPP synthase appears to be regulated in a sterol-independent manner. The gene encoding human GGPP synthase has been cloned and GGPP synthase mRNA is expressed ubiquitously, with highest levels found in the testis. In rat thyroid cells, GGPP synthase expression is upregulated, coincident with cellular proliferation, following the stimulation of cells with thyrotropin and insulin. In addition, GGPP synthase was first cloned in mice as a result of its identification as one of the genes upregulated in ob/ob mice, a model of obesity and insulin resistance. Thus alterations in levels of GGPP appear important in both physiological and pathophysiological processes and a method to experimentally manipulate intracellular GGPP levels would provide further understanding of these processes.

Nitrogen-containing bisphosphonates, including alendronate, pamidronate, and zoledronate, have been shown to inhibit FPP synthase. This class of drugs is used to inhibit bone resorption in a number of diseases, including osteoporosis, tumor-associated bone disease, and Paget's disease. The aminobisphosphonates, by depleting cells of both FPP and GGPP, prevent the farnesylation and geranylgeranylation of small GTPases. It appears that the depletion of GGPP, with subsequent diminished protein geranylgeranylation is the critical mechanism underlying the effects of the aminobisphosphonates. In specific, it has been suggested that the loss of activity of geranylgeranylated proteins, such as cdc42, Rac, and Rho in osteoclasts, is directly related to the antiresorptive effects as restoration of geranylgeranylation blocks the effects of the aminobisphosphonates on osteoclasts. The currently clinically used bisphosphonates may have additional therapeutic uses as it was recently demonstrated that alendronate inhibits the invasion of both prostate and breast cancer cells. Finally, a number of nitrogen-containing bisphosphonates have also been shown to inhibit the growth of parasites, including *Trypanosoma brucei, Leishmania donovani,* and *Plasmodium falciparum.*

There are no GGPP synthase inhibitors currently available for clinical use. There have been several reports of compounds, both synthetic and natural, which inhibit GGPP synthase. The potency and selectivity of these compounds for GGPP synthase vs. FPP synthase varies significantly. Given the findings discussed above, there is considerable interest in the development of specific GGPP synthase inhibitors.

It would be predicted that selective GGPP synthase inhibitors could be used for the same therapeutic applications as FPP synthase inhibitors as novel anticancer agents, with the added advantage of more specifically affecting the essential downstream targets. That is, while levels of GGPP would be depleted, synthesis of FPP would not be affected, hence the pathways utilizing FPP (e.g., sterol synthesis, dolichol synthesis) would be preserved.

GGPP synthase inhibitors would also serve as important tools which could be used in studies addressing the significance of isoprenoid intermediate pool size, flux through the isoprenoid biosynthetic pathway, hierarchy among geranylgeranylated proteins, and regulatory properties of endogenous isoprenoid pyrophosphates. In specific, while both FPP and GGPP have been shown to regulate the expression of a number of small GTPases, the relative contribution of the two isoprenoid species has yet to be fully determined Thus the availability of GGPP synthase inhibitors would provide for novel experimental approaches and improved therapeutic strategies.

In summary there is currently a need for GGPP synthase inhibitors. Such compounds would be useful as chemical tools to ascertain the importance of GGPP in a number of cellular processes. Additionally, they would be anticipated to be useful: 1) as antiproliferative agents for the treatment of cancer (based on analogy with the FPTase inhibitors), 2) to inhibit testicular function and thus have activity to decrease male fertility (based on high levels of GGPS in testes), 3) to treat parasitic infections (e.g. malaria), and 4) to treat insulin resistance and obesity based on the ob/ob mouse model of insulin resistance and obesity. They would also be anticipated to be useful in the treatment of a number of parasitic diseases and to have potent osteoclast inhibitory function and to be useful in the prevention and treatment of osteoporosis.

SUMMARY OF CERTAIN EMBODIMENTS OF THE INVENTION

The present invention provides compounds that act as GGPP synthase inhibitors. Accordingly there is provided a compound of the invention which is a compound of formula I or formula II:

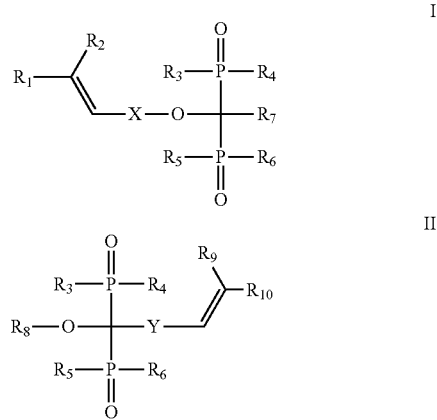

wherein:
X is $(C_1-C_6)$alkyl;
Y is $(C_1-C_6)$alkyl;
$R_1$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

$R_2$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

each $R_3$, $R_4$, $R_5$, and $R_6$ is independently OH or $(C_1-C_6)$alkoxy;

$R_7$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, aryl, heteroaryl, or $S(O)_2NR_cR_d$;

$R_8$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, aryl, heteroaryl, or $S(O)_2NR_cR_d$;

$R_9$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

$R_{10}$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_q$, and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

each $R_a$ and $R_b$ is independently H, $(C_1-C_6)$alkyl, or aryl; or $R_a$ and $R_b$ together with the nitrogen to which they are attached form a pyrrolidino, piperidino, morpholino, or thiomorpholino ring;

each $R_c$ and $R_d$ is independently H, $(C_1-C_6)$alkyl, or aryl; or $R_c$ and $R_d$ together with the nitrogen to which they are attached form a pyrrolidino, piperidino, morpholino, or thiomorpholino ring;

each $R_m$ and $R_n$ is independently H, $(C_1-C_6)$alkyl, or aryl; or $R_m$ and $R_n$ together with the nitrogen to which they are attached form a pyrrolidino, piperidino, morpholino, or thiomorpholino ring;

each $R_p$ and $R_q$ is independently H, $(C_1-C_6)$alkyl, or aryl; or $R_p$ and $R_q$ together with the nitrogen to which they are attached form a pyrrolidino, piperidino, morpholino, or thiomorpholino ring; and wherein any aryl of $R_a$, $R_b$, $R_c$, $R_d$, $R_m$, $R_n$, $R_p$ or $R_q$ is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_sR_t$, or $S(O)_2NR_sR_t$ wherein each $R_s$ and $R_t$ is independently H or $(C_1-C_6)$alkyl;

or a salt thereof.

Also provided is a compound of the invention which is a compound of formula Ia or formula IIa:

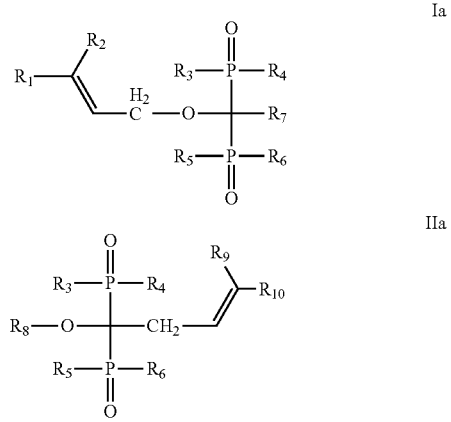

wherein:
$R_1$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

$R_2$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

each $R_3$, $R_4$, $R_5$, and $R_6$ is independently OH or $(C_1-C_6)$ alkoxy;

$R_7$ is a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

$R_8$ is a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

$R_9$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

$R_{10}$ is H or a saturated or unsaturated $(C_1-C_{20})$alkyl chain that optionally comprises one or more aryl or heteroaryl rings in the chain wherein $(C_5-C_{20})$alkyl is optionally substituted with one or more halo cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$;

each $R_a$ and $R_b$ is independently H, $(C_1-C_6)$alkyl, or aryl; or $R_a$ and $R_b$ together with the nitrogen to which they are attached form a pyrrolidino, piperidino, morpholino, or thiomorpholino ring;

each $R_c$ and $R_d$ is independently H, $(C_1-C_6)$alkyl, or aryl; or $R_c$ and $R_d$ together with the nitrogen to which they are attached form a pyrrolidino, piperidino, morpholino, or thiomorpholino ring;

each $R_m$ and $R_n$ is independently H, $(C_1-C_6)$alkyl, or aryl; or $R_m$ and $R_n$ together with the nitrogen to which they are attached form a pyrrolidino, piperidino, morpholino, or thiomorpholino ring;

each $R_p$ and $R_q$ is independently H, $(C_1-C_6)$alkyl, or aryl; or $R_p$ and $R_q$ together with the nitrogen to which they are attached form a pyrrolidino, piperidino, morpholino, or thiomorpholino ring; and wherein any aryl of $R_a$, $R_b$, $R_c$, $R_d$, $R_m$, $R_n$, $R_p$ or $R_q$ is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_sR_t$, or $S(O)_2NR_sR_t$ wherein each $R_s$ and $R_t$ is independently H or $(C_1-C_6)$alkyl;

or a salt thereof.

Also provided are pharmaceutical compositions comprising compounds as described herein, together with a pharmaceutically acceptable carrier. Also provided are methods for inhibiting geranylgeranyl pyrophosphate synthase comprising contacting the geranylgeranyl pyrophosphate synthase in vitro or in vivo with an effective inhibitory amount of a compound as described herein. Also provided are methods for treating diseases comprising administering to an animal (e.g. a mammal such as a human) in need of such treatment an effective amount of a compound as described herein, or equivalently, the use of compounds as described herein to prepare a medicament useful for modulating diseases, or the use of compounds in disease treatment.

DETAILED DESCRIPTION

Figure 1:
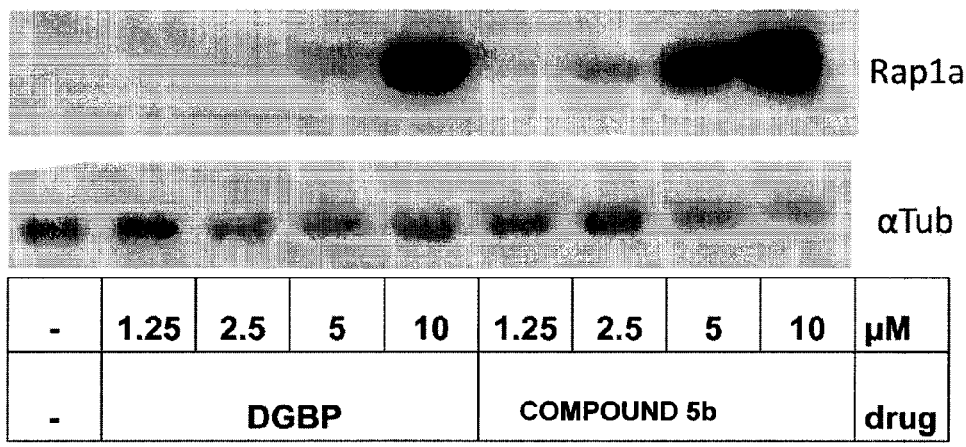
FIG. 1 shows a Western Blot illustrating a bioactivities comparison for Compound 5b and digeranyl bisphosphonate (DGBP) in Test A.

Provided herein are compounds of Formula I and II, as disclosed above.

In certain embodiments, the compound is a compound of formula I, or a salt thereof.

In certain embodiments, the compound is a compound of formula II, or a salt thereof.

Also provided are compounds of Formula I wherein m is an integer from 1 to 2.

Also provided are compounds of Formula I wherein $R_1$ is an unsaturated $(C_1-C_{20})$alkyl chain optionally substituted with one or more halo, cyano, nitro, carboxy, trifluoromethyl, trifluoromethoxy, aryl, heteroaryl, $NR_mR_n$, or $S(O)_2NR_pR_q$. In further embodiments, the alkyl chain is a $(C_5-C_{20})$alkyl chain, $(C_5-C_{15})$alkyl chain, or $(C_5-C_{10})$alkyl chain. Also provided are compounds of Formula I wherein $R_1$ is an unsaturated $(C_5-C_{20})$alkyl chain. In certain embodiments, $R_1$ is an unsaturated $(C_5-C_{15})$alkyl chain. In certain embodiments, $R_1$ is an unsaturated $(C_5-C_{10})$alkyl chain. In certain embodiments, $R_1$ is

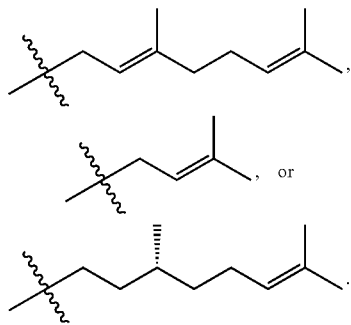

In certain embodiments, $R_1$ is

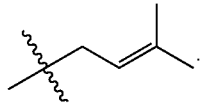 [SMILES: *CC=C(C)C]

Also provided is an alternative embodiment in which any of these embodiments may be substituted on a terminal carbon with hydroxy or a five-membered heterocycloalkyl. In further embodiments, the five-membered heterocycloalkyl contains from one to four heteroatoms chosen from O, S, and N. In further embodiments, the five-membered heterocycloalkyl contains from one to two heteroatoms chosen from O, S, and N. In further embodiments, the five-membered heterocycloalkyl is aromatic, i.e., a heteroaryl.

In certain embodiments of Formula I, $R_1$ is a saturated or unsaturated $(C_1-C_{20})$alkyl chain that comprises one or more aryl rings in the chain. In certain embodiments of Formula I, $R_1$ is

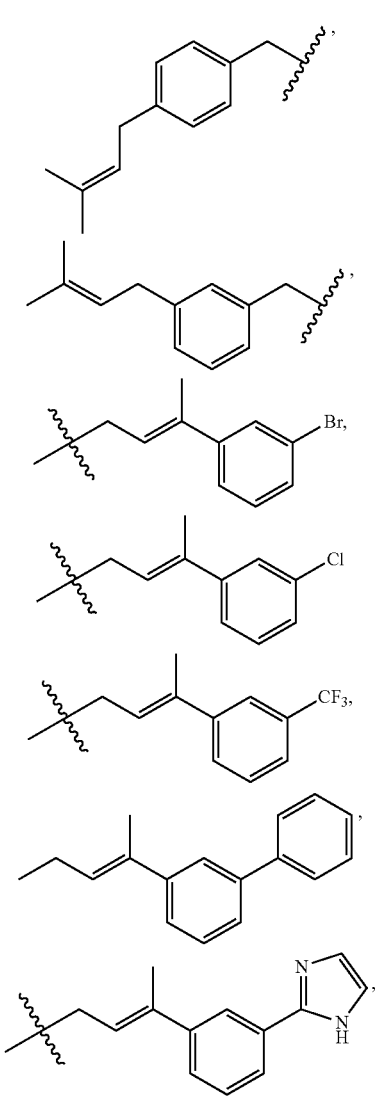

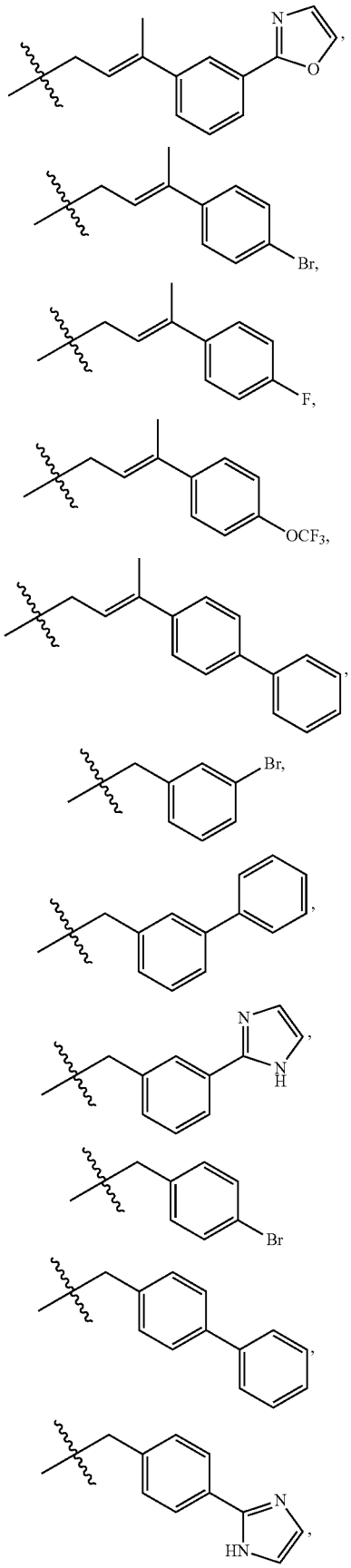

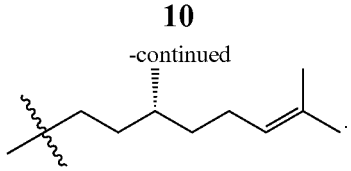

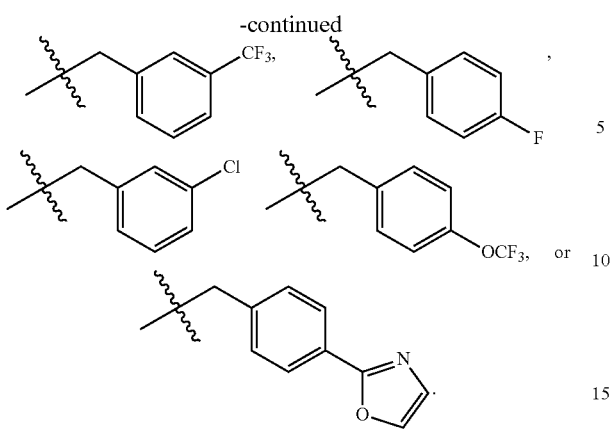

In certain embodiments of Formula I, $R_1$ is a unsaturated ($C_5$-$C_{20}$)alkyl chain that comprises a heteroaryl ring in the chain. In further embodiments, the heteroaryl ring is indolyl.

In further embodiments, $R_1$ is

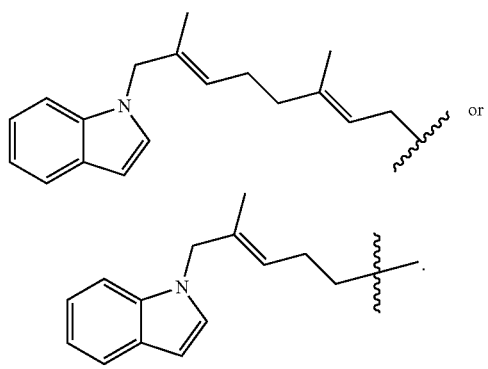

In certain embodiments of Formula I, $R_2$ is H or methyl. In certain embodiments of Formula I, $R_2$ is methyl.

In certain embodiments of Formula I, m is 1. In certain embodiments of Formula I, m is 2.

Also provided are compounds of Formula I wherein $R_7$ is an unsaturated ($C_1$-$C_{20}$)alkyl chain optionally substituted with one or more halo, cyano, nitro, carboxy, trifluoromethyl, trifluoromethoxy, aryl, heteroaryl, $NR_mR_n$, or $S(O)_2NR_pR_q$. In further embodiments, the alkyl chain is a ($C_5$-$C_{20}$)alkyl chain, ($C_5$-$C_{15}$)alkyl chain, or ($C_5$-$C_{10}$)alkyl chain. Also provided are compounds according to any of the above embodiments wherein $R_7$ is a saturated or unsaturated ($C_1$-$C_{20}$)alkyl chain. In further embodiments, $R_7$ is a saturated or unsaturated ($C_5$-$C_{20}$)alkyl chain. In further embodiments, $R_7$ is a saturated or unsaturated ($C_5$-$C_{15}$)alkyl chain. In further embodiments, $R_7$ is a saturated or unsaturated ($C_5$-$C_{10}$)alkyl chain. In further embodiments, $R_7$ is

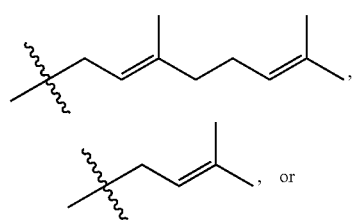

In certain embodiments, $R_7$ is

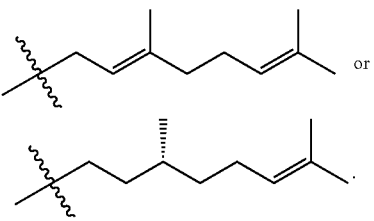

Also provided is an alternative embodiment in which any of these embodiments may be substituted on a terminal carbon with hydroxy or a five-membered heterocycloalkyl. In further embodiments, the five-membered heterocycloalkyl contains from one to four heteroatoms chosen from O, S, and N. In further embodiments, the five-membered heterocycloalkyl contains from one to two heteroatoms chosen from O, S, and N. In further embodiments, the five-membered heterocycloalkyl is aromatic, i.e., a heteroaryl.

Also provided are compounds according to any of the above embodiments wherein $R_7$ is a saturated or unsaturated ($C_1$-$C_{20}$)alkyl chain that comprises one or more aryl or heteroaryl rings in the chain. In further embodiments, $R_7$ is

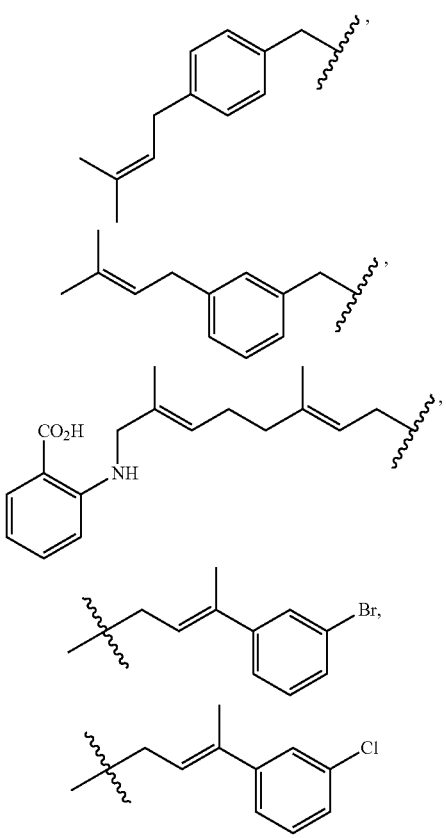

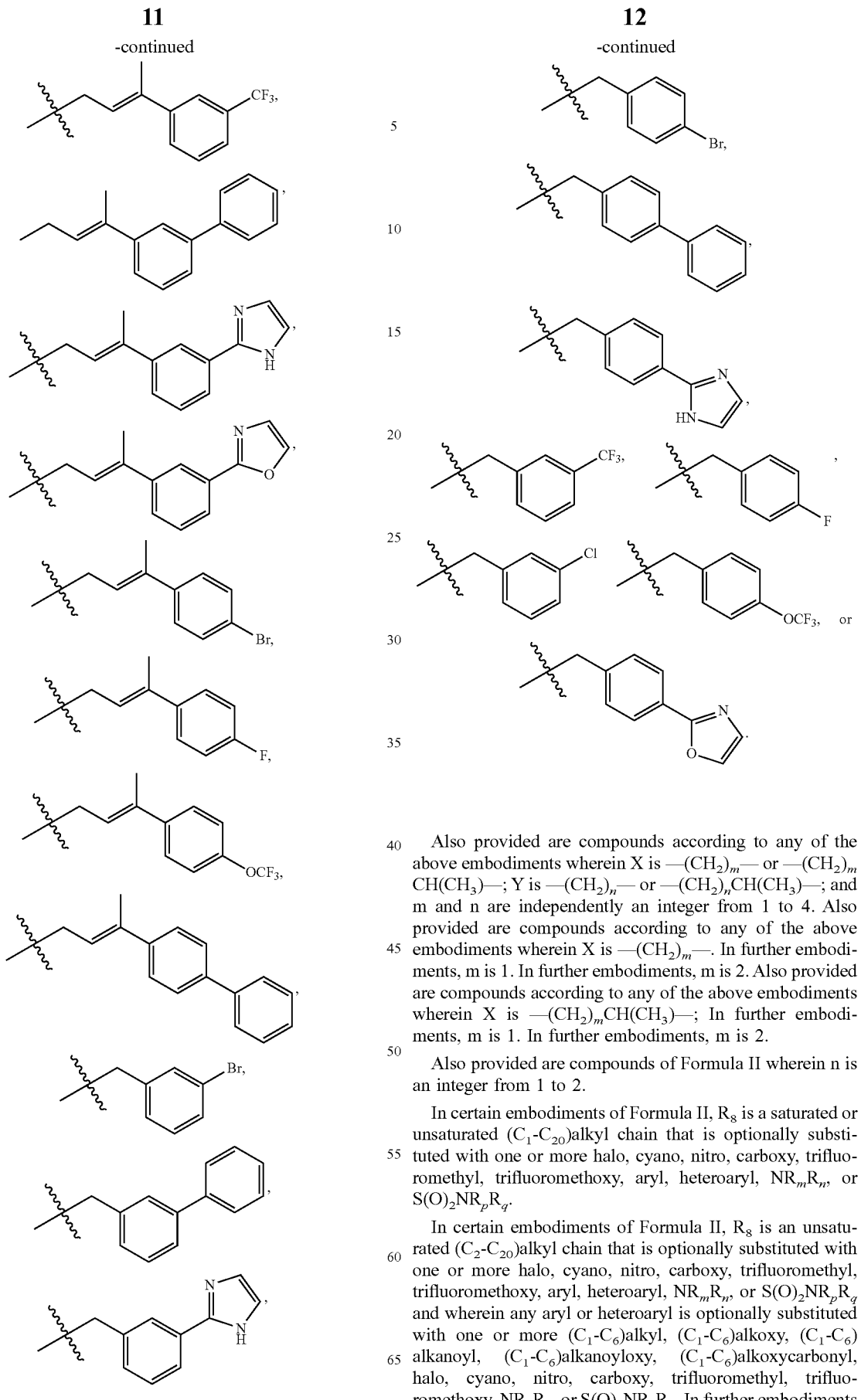

Also provided are compounds according to any of the above embodiments wherein X is —(CH$_2$)$_m$— or —(CH$_2$)$_m$CH(CH$_3$)—; Y is —(CH$_2$)$_n$— or —(CH$_2$)$_n$CH(CH$_3$)—; and m and n are independently an integer from 1 to 4. Also provided are compounds according to any of the above embodiments wherein X is —(CH$_2$)$_m$—. In further embodiments, m is 1. In further embodiments, m is 2. Also provided are compounds according to any of the above embodiments wherein X is —(CH$_2$)$_m$CH(CH$_3$)—; In further embodiments, m is 1. In further embodiments, m is 2.

Also provided are compounds of Formula II wherein n is an integer from 1 to 2.

In certain embodiments of Formula II, R$_8$ is a saturated or unsaturated (C$_1$-C$_{20}$)alkyl chain that is optionally substituted with one or more halo, cyano, nitro, carboxy, trifluoromethyl, trifluoromethoxy, aryl, heteroaryl, NR$_m$R$_n$, or S(O)$_2$NR$_p$R$_q$.

In certain embodiments of Formula II, R$_8$ is an unsaturated (C$_2$-C$_{20}$)alkyl chain that is optionally substituted with one or more halo, cyano, nitro, carboxy, trifluoromethyl, trifluoromethoxy, aryl, heteroaryl, NR$_m$R$_n$, or S(O)$_2$NR$_p$R$_q$ and wherein any aryl or heteroaryl is optionally substituted with one or more (C$_1$-C$_6$)alkyl, (C$_1$-C$_6$)alkoxy, (C$_1$-C$_6$)alkanoyl, (C$_1$-C$_6$)alkanoyloxy, (C$_1$-C$_6$)alkoxycarbonyl, halo, cyano, nitro, carboxy, trifluoromethyl, trifluoromethoxy, NR$_a$R$_b$, or S(O)$_2$NR$_c$R$_d$. In further embodiments of Formula II, $R_8$ is an unsaturated $(C_2-C_{20})$alkyl chain. In further embodiments of Formula II, $R_8$ is

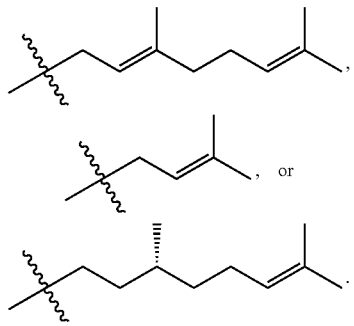

In certain embodiments, $R_8$ is

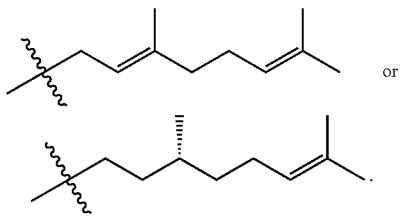

Also provided is an alternative embodiment in which any of the preceding three embodiments may be substituted on a terminal carbon with hydroxy or a five-membered heterocycloalkyl. In further embodiments, the five-membered heterocycloalkyl contains from one to four heteroatoms chosen from O, S, and N. In further embodiments, the five-membered heterocycloalkyl contains from one to two heteroatoms chosen from O, S, and N. In further embodiments, the five-membered heterocycloalkyl is aromatic, i.e., a heteroaryl.

In certain embodiments of Formula II, $R_8$ is a saturated $(C_1-C_{20})$alkyl chain that comprises one or more aryl or heteroaryl rings in the chain wherein $(C_1-C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$. In further embodiments of Formula II, $R_8$ is

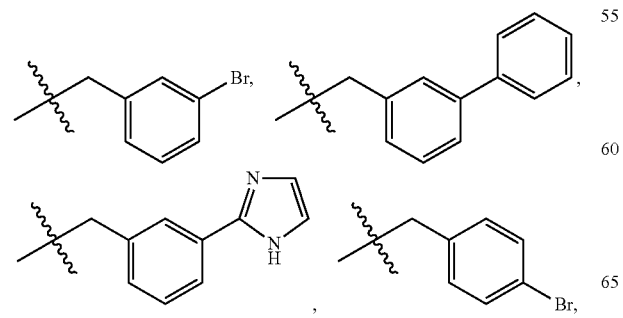

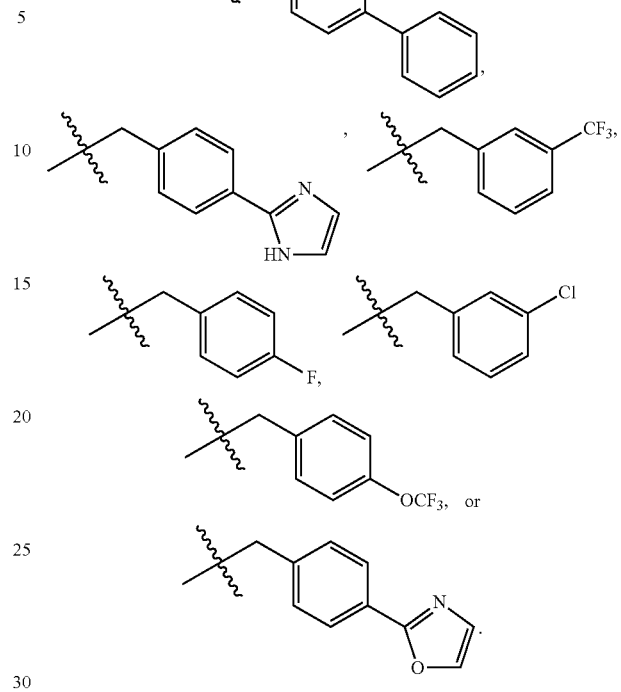

In certain embodiments of Formula II, $R_8$ is a saturated $(C_1-C_{20})$alkyl chain. In certain embodiments of Formula II, $R_8$ is an unsaturated $(C_1-C_{20})$alkyl chain that comprises one or more aryl or heteroaryl rings in the chain wherein $(C_1-C_{20})$alkyl is optionally substituted with one or more halo, cyano, nitro, carboxy, trifluoromethyl, trifluoromethoxy, aryl, heteroaryl, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$.

In certain embodiments of Formula II, $R_8$ is

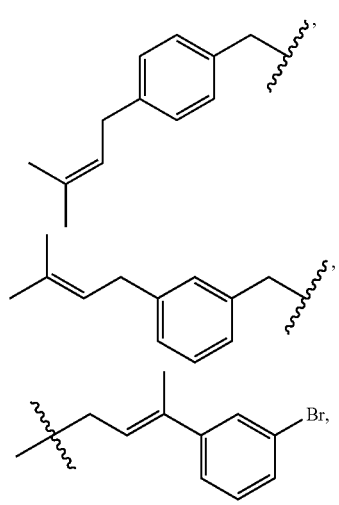

15
-continued
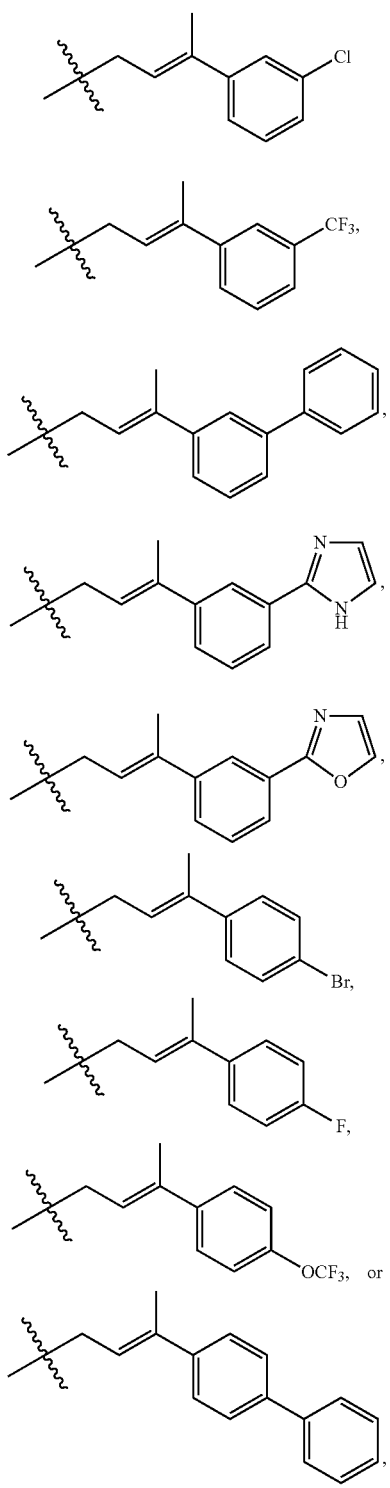
16
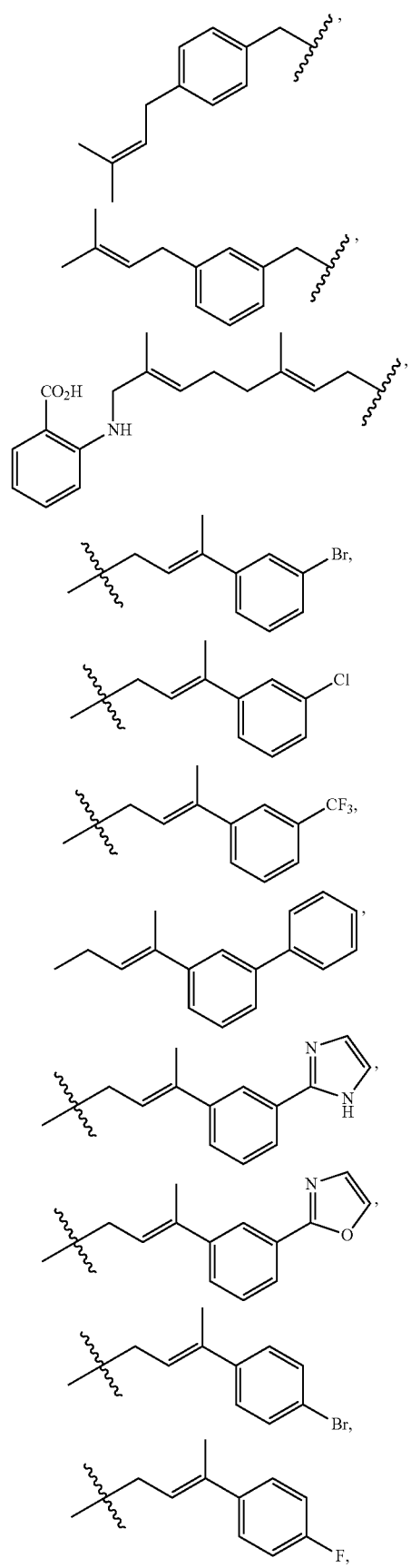
Also provided are compounds according to any of the above embodiments wherein $R_9$ is an unsaturated $(C_5-C_{20})$ alkyl chain.
Also provided are compounds according to any of the above embodiments wherein $R_9$ is a saturated or unsaturated $(C_5-C_{20})$alkyl chain that comprises one or more aryl rings in the chain. In further embodiments, $R_9$ is -continued

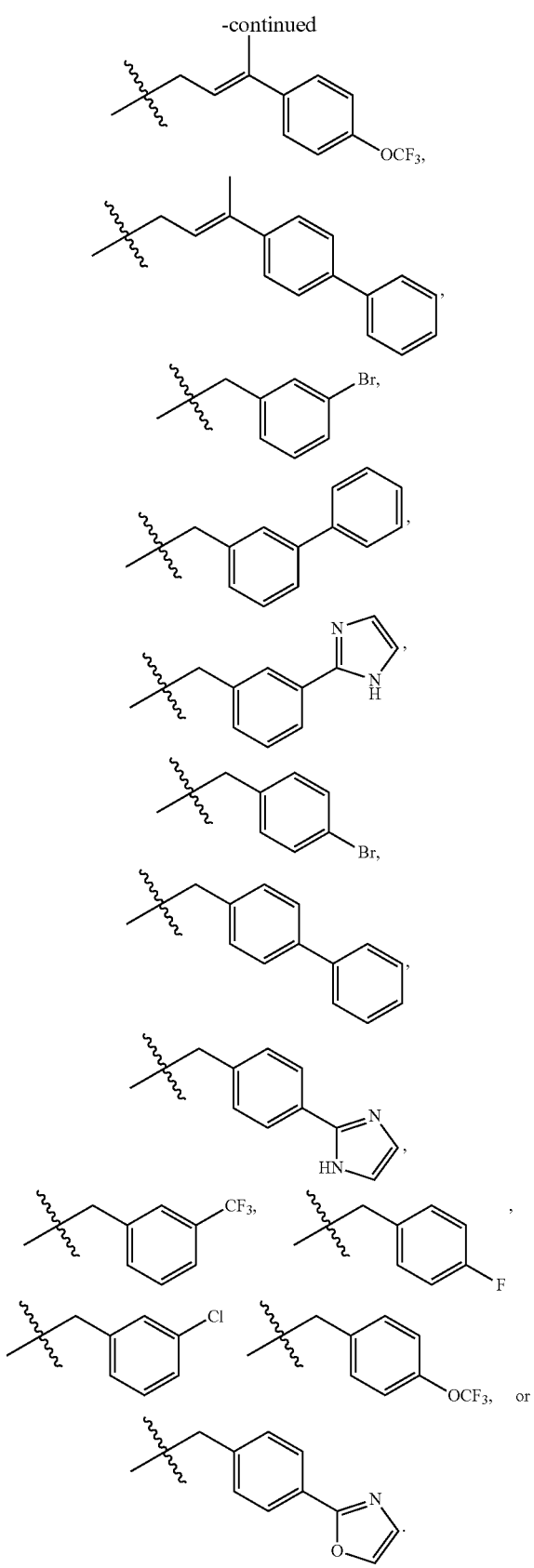

Also provided are compounds according to any of the above embodiments wherein $R_9$ is an unsaturated ($C_5$-$C_{20}$) alkyl chain that comprises a heteroaryl ring in the chain. In further embodiments, the heteroaryl ring is indolyl. In further embodiments, $R_9$ is

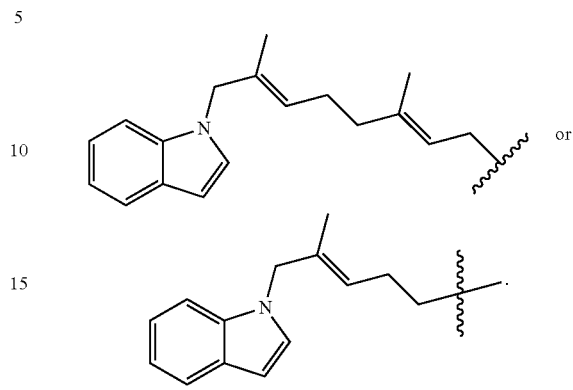

Also provided are compounds of Formula II wherein $R_9$ is an unsaturated ($C_1$-$C_{20}$)alkyl chain optionally substituted with one or more halo, cyano, nitro, carboxy, trifluoromethyl, trifluoromethoxy, aryl, heteroaryl, $NR_mR_n$, or $S(O)_2$ $NR_pR_q$. In further embodiments, the alkyl chain is a ($C_5$-$C_{20}$)alkyl chain, ($C_5$-$C_{15}$)alkyl chain, or ($C_5$-$C_{10}$)alkyl chain. Also provided are compounds according to any of the above embodiments wherein $R_9$ is an unsaturated ($C_1$-$C_{20}$) alkyl chain. In further embodiments, $R_9$ is an unsaturated ($C_5$-$C_{20}$)alkyl chain. In further embodiments, $R_9$ is an unsaturated ($C_5$-$C_{15}$)alkyl chain. In further embodiments, $R_9$ is an unsaturated ($C_5$-$C_{10}$)alkyl chain. In further embodiments, $R_9$ is:

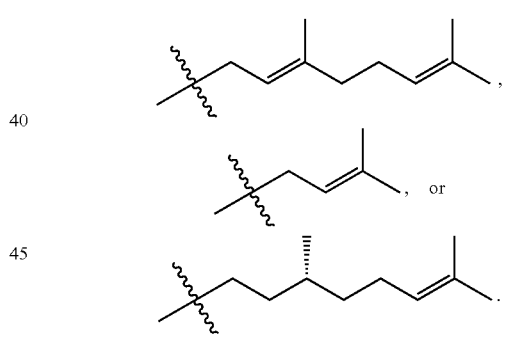

In certain embodiments, $R_9$ is

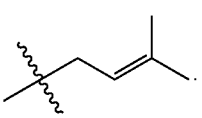 [SMILES: *CC=C(C)C]

Also provided is an alternative embodiment in which any of these embodiments may be substituted on a terminal carbon with hydroxy or a five-membered heterocycloalkyl. In further embodiments, the five-membered heterocycloalkyl contains from one to four heteroatoms chosen from O, S, and N. In further embodiments, the five-membered heterocycloalkyl contains from one to two heteroatoms chosen from O, S, and N. In further embodiments, the five-membered heterocycloalkyl is aromatic, i.e., a heteroaryl.

Also provided are compounds according to any of the above embodiments wherein $R_{10}$ is H or methyl. Also provided are compounds according to any of the above embodiments wherein $R_{10}$ is methyl.

Also provided are compounds according to any of the above embodiments wherein Y is $-(CH_2)_n-$. In further embodiments, n is 1. In further embodiments, n is 2.

Also provided are compounds according to any of the above embodiments wherein Y is $-(CH_2)_nCH(CH_3)-$; In further embodiments, n is 1. In further embodiments, n is 2.

Also provided are compounds according to any of the above embodiments wherein $R_3$, $R_4$, $R_5$ and $R_6$ are each OH. Also provided are compounds according to any of the above embodiments wherein $R_3$, $R_4$, $R_5$ and $R_6$ are each $(NaO)_2O$. Also provided are compounds according to any of the above embodiments wherein $R_3$, $R_4$, $R_5$ and $R_6$ are each alkoxy. Also provided are compounds according to any of the above embodiments wherein $R_3$, $R_4$, $R_5$ and $R_6$ are each ethoxy.

Also provided is a compound selected from:

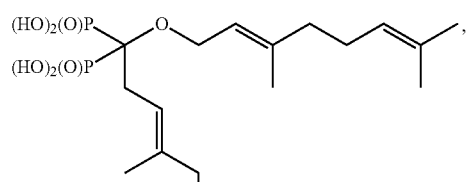

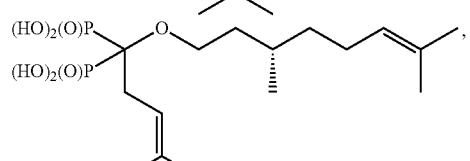

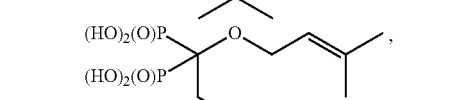

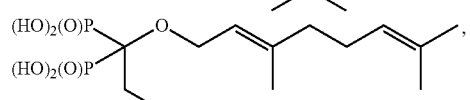

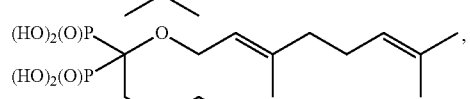

-continued

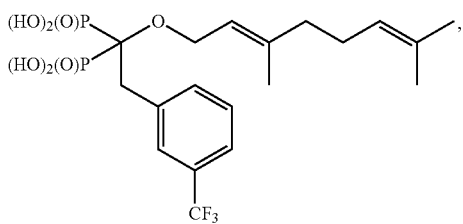

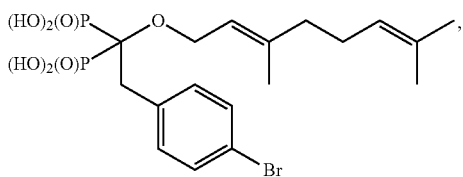

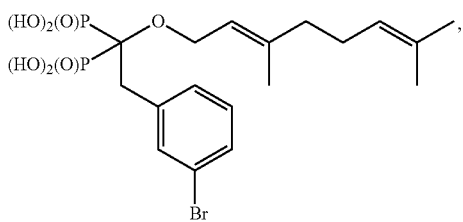

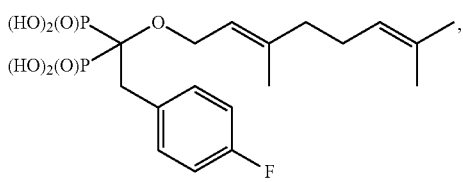

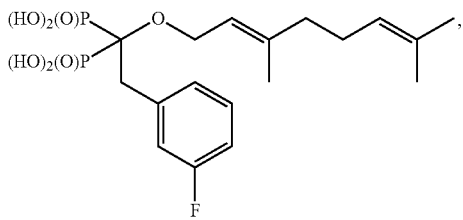

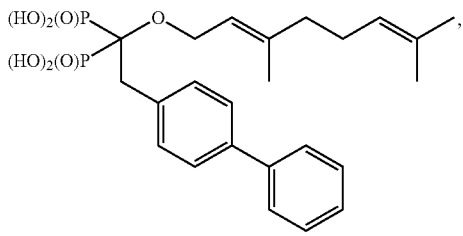

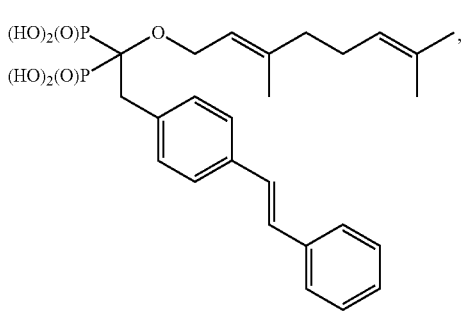

-continued
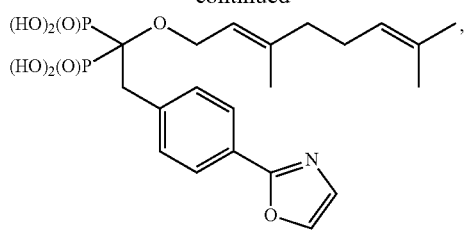
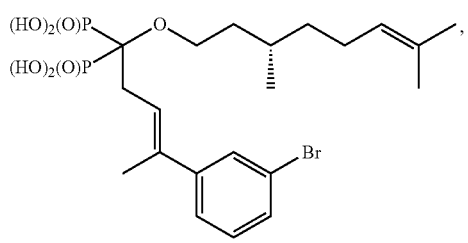
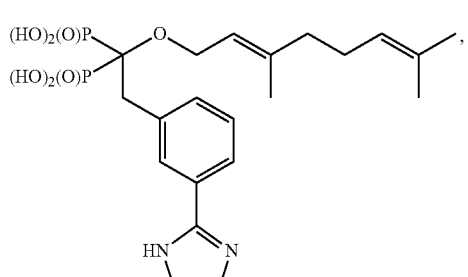
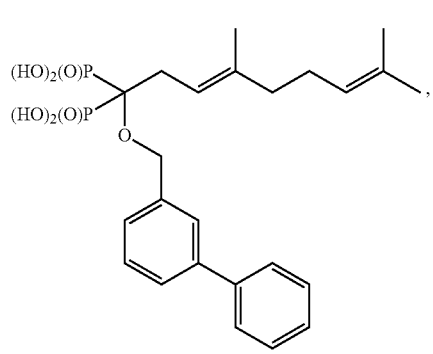
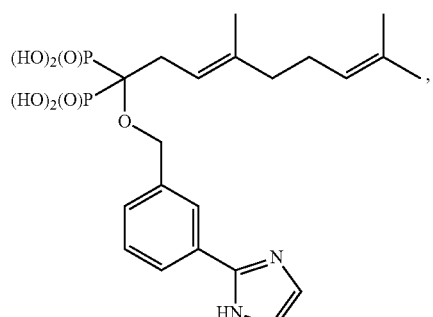
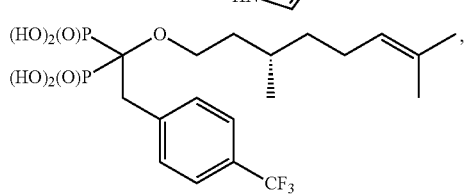
-continued
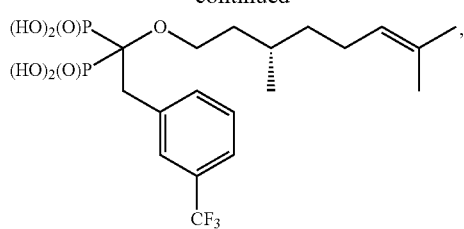
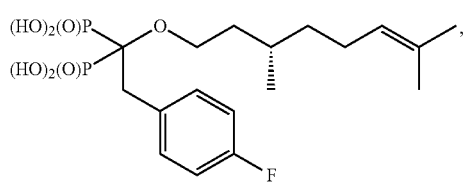
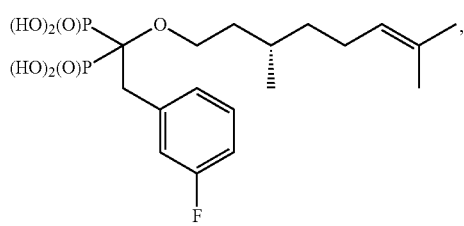
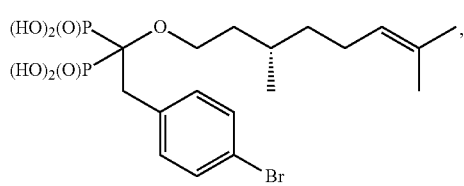
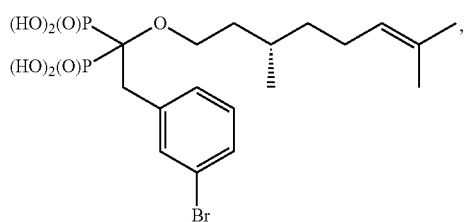
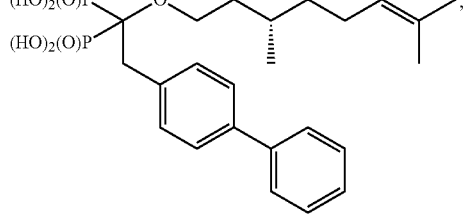
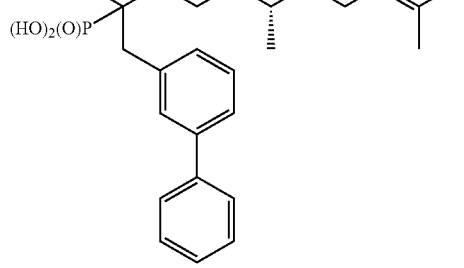

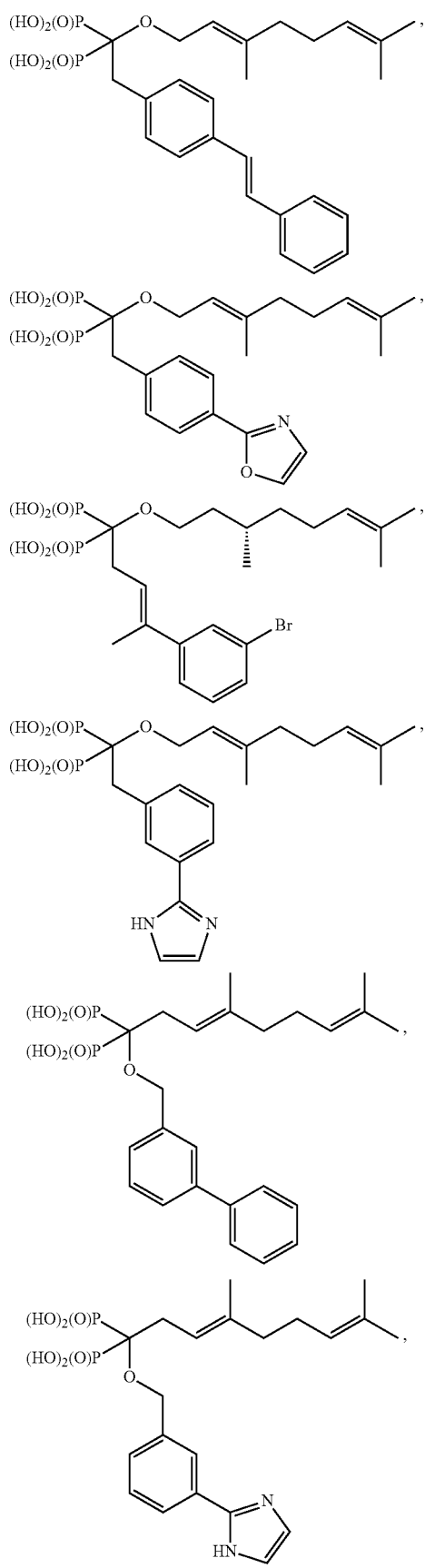
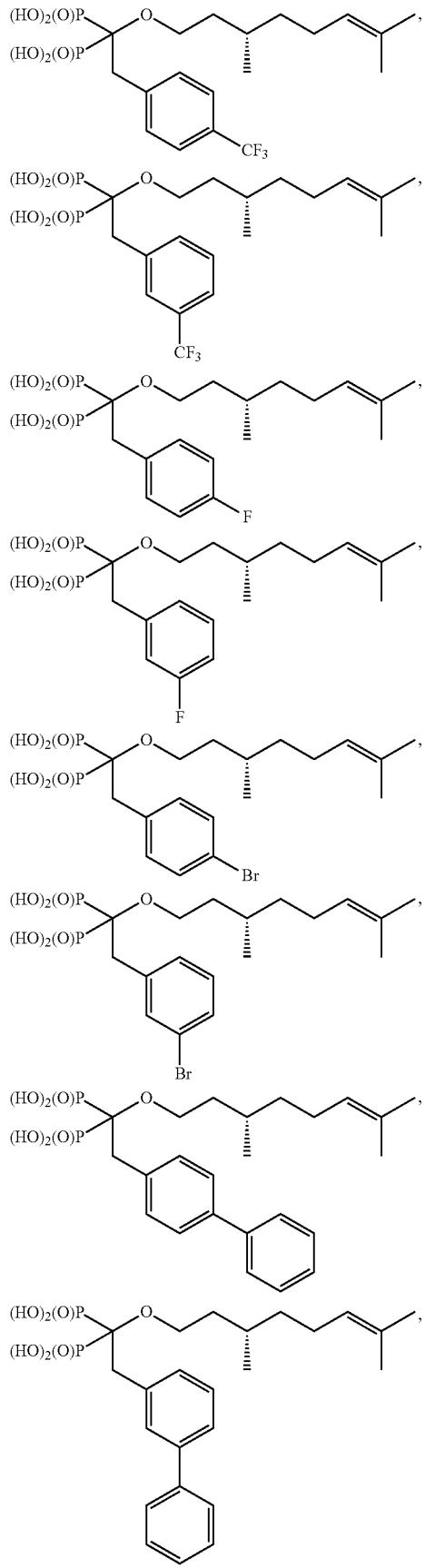

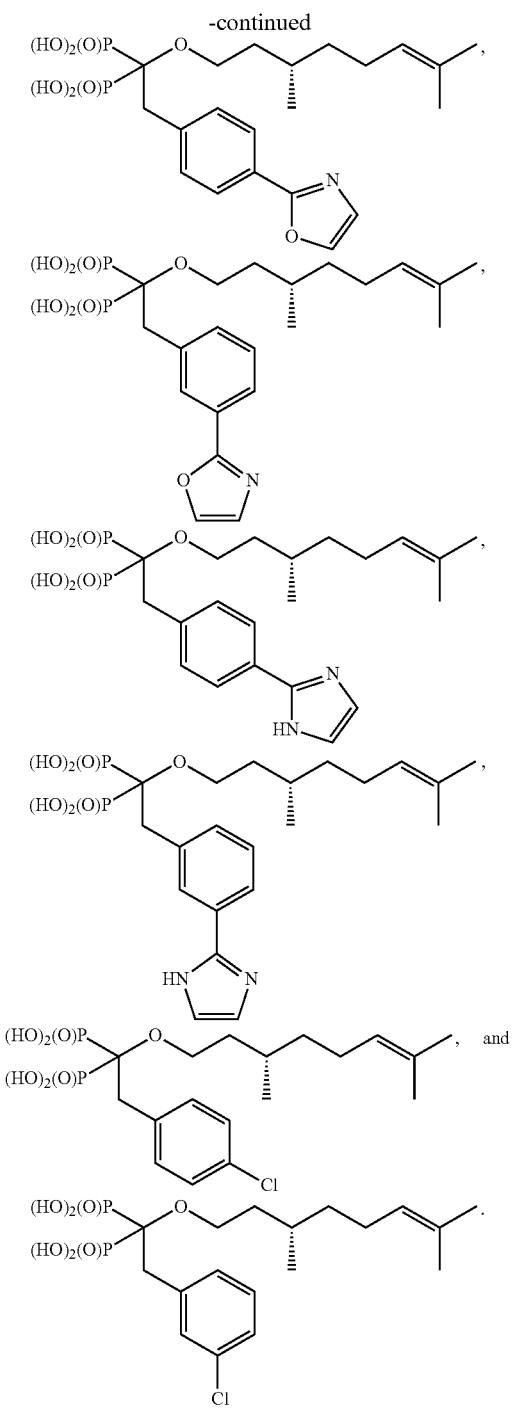

and salts thereof.

Also provided are compounds of Formula I wherein:

$R_1$ is a saturated or unsaturated $(C_1-C_{20})$alkyl chain that optionally comprises one or more aryl or heteroaryl rings in the chain wherein $(C_1-C_{20})$alkyl is optionally substituted with one to three halo, cyano, nitro, carboxy, trifluoromethyl, trifluoromethoxy, $NH_2$, or $S(O)_2NH_2$, and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

$R_2$ is H or methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, aryl, heteroaryl, or $S(O)_2NH_2$;

or a salt thereof.

Also provided are compounds of Formula I wherein:

$R_1$ is a saturated or unsaturated $(C_1-C_{20})$alkyl chain optionally substituted with one to three halo, cyano, nitro, carboxy, trifluoromethyl, trifluoromethoxy, $NH_2$, or $S(O)_2NH_2$;

$R_2$ is H or methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, aryl, heteroaryl, or $S(O)_2NH_2$;

or a salt thereof.

Also provided are compounds of Formula I wherein:

$R_1$ is a saturated or unsaturated $(C_1-C_{20})$alkyl chain;

$R_2$ is methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain that comprises one or more aryl or heteroaryl rings in the chain wherein any aryl or heteroaryl is optionally substituted with one or two $(C_1-C_6)$alkyl, halo, trifluoromethyl, aryl, heteroaryl, or trifluoromethoxy;

or a salt thereof.

Also provided are compounds of Formula I wherein:

$R_1$ is a saturated or unsaturated $(C_1-C_{20})$alkyl chain comprising one or more aryl or heteroaryl rings in the chain wherein $R_2$ is H or methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, aryl, heteroaryl, or $S(O)_2NH_2$;

or a salt thereof.

Also provided are compounds of Formula I wherein:

X is —$(CH_2)_m$— or —$(CH_2)_mCH(CH_3)$—;

m is an integer from 1 to 2;

$R_1$ is a saturated or unsaturated $(C_1-C_{20})$alkyl chain that optionally comprises one or more aryl or heteroaryl rings in the chain wherein $(C_1-C_{20})$alkyl is optionally substituted with one to three halo, cyano, nitro, carboxy, trifluoromethyl, trifluoromethoxy, $NH_2$, or $S(O)_2NH_2$, and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

$R_2$ is H or methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

or a salt thereof.

Also provided are compounds of Formula I wherein:

X is $-(CH_2)_m-$ or $-(CH_2)_mCH(CH_3)-$;

m is an integer from 1 to 2;

$R_1$ is a saturated or unsaturated $(C_1-C_{20})$alkyl chain optionally substituted with one to three halo, cyano, nitro, carboxy, trifluoromethyl, trifluoromethoxy, $NH_2$, or $S(O)_2NH_2$;

$R_2$ is H or methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

or a salt thereof.

Also provided are compounds of Formula I wherein:

X is $-(CH_2)_m-$ or $-(CH_2)_mCH(CH_3)-$;

m is an integer from 1 to 2;

$R_1$ is a saturated or unsaturated $(C_1-C_{20})$alkyl chain;

$R_2$ is H or methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain;

or a salt thereof.

Also provided are compounds according to any of the above embodiments wherein $R_1$ is a saturated or unsaturated $(C_5-C_{20})$alkyl chain. Also provided are compounds according to any of the above embodiments wherein $R_1$ is a saturated or unsaturated $(C_5-C_{15})$alkyl chain. Also provided are compounds according to any of the above embodiments wherein $R_1$ is a saturated or unsaturated $(C_5-C_{10})$alkyl chain.

Also provided are compounds of Formula I wherein:

X is $-(CH_2)_m-$ or $-(CH_2)_mCH(CH_3)-$;

m is an integer from 1 to 2;

$R_1$ is a saturated or unsaturated $(C_1-C_{20})$alkyl chain;

$R_2$ is methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain that comprises one or more aryl or heteroaryl rings in the chain wherein any aryl or heteroaryl is optionally substituted with one or two $(C_1-C_6)$alkyl, halo, trifluoromethyl, or trifluoromethoxy; or a salt thereof.

Also provided are compounds of Formula I wherein:

X is $-(CH_2)_m-$ or $-(CH_2)_mCH(CH_3)-$;

m is an integer from 1 to 2;

$R_1$ is a saturated or unsaturated $(C_1-C_{20})$alkyl chain comprising one or more aryl or heteroaryl rings in the chain wherein $R_2$ is H or methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

or a salt thereof.

Also provided are compounds of Formula I wherein:

X is $-(CH_2)_m-$ or $-(CH_2)_mCH(CH_3)-$;

m is an integer from 1 to 2;

$R_1$ is a saturated or unsaturated $(C_1-C_{20})$alkyl chain comprising one or more aryl or heteroaryl rings in the chain wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

$R_2$ is H or methyl;

each $R_3$, $R_4$, $R_5$, and $R_6$ is independently OH, or $(C_1-C_6)$alkoxy;

$R_7$ is a saturated or unsaturated $(C_1-C_{20})$alkyl chain;

or a salt thereof.

Also provided are compounds according to any of the above embodiments wherein X is $-(CH_2)_m-$. In further embodiments, m is 1. In further embodiments, m is 2.

Also provided are compounds according to any of the above embodiments wherein X is $-(CH_2)_mCH(CH_3)-$; In further embodiments, m is 1. In further embodiments, m is 2.

Also provided are compounds of Formula II wherein:

each $R_3$, $R_4$, $R_5$, and $R_6$ is independently OH, or $(C_1-C_6)$alkoxy;

$R_8$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

$R_9$ is a saturated or unsaturated $(C_1-C_{20})$alkyl chain that optionally comprises one or more aryl or heteroaryl rings in the chain wherein $(C_1-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, aryl or heteroaryl, or $S(O)_2NH_2$;

$R_{10}$ is H or methyl;

or a salt thereof.

Also provided are compounds of Formula II wherein:
each $R_3$, $R_4$, $R_5$, and $R_6$ is independently OH, or $(C_1-C_6)$alkoxy;

$R_8$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, aryl or heteroaryl, or $S(O)_2NH_2$;

$R_9$ is H or a saturated or unsaturated $(C_1-C_{20})$alkyl chain optionally substituted with one or more halo, cyano, nitro, carboxy, trifluoromethyl, trifluoromethoxy, $NH_2$, or $S(O)_2NH_2$;

$R_{10}$ is H or methyl;

or a salt thereof.

Also provided are compounds of Formula II wherein:
Y is —$(CH_2)_m$— or —$(CH_2)_mCH(CH_3)$—;
n is an integer from 1 to 2;
each $R_3$, $R_4$, $R_5$, and $R_6$ is independently OH, or $(C_1-C_6)$alkoxy;

$R_8$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

$R_9$ is a saturated or unsaturated $(C_1-C_{20})$alkyl chain that optionally comprises one or more aryl or heteroaryl rings in the chain wherein $(C_1-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

$R_{10}$ is H or methyl;

or a salt thereof.

Also provided are compounds of Formula II wherein:
Y is —$(CH_2)_m$— or —$(CH_2)_mCH(CH_3)$—;
n is an integer from 1 to 2;
each $R_3$, $R_4$, $R_5$, and $R_6$ is independently OH, or $(C_1-C_6)$alkoxy;

$R_8$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

$R_9$ is H or a saturated or unsaturated $(C_1-C_{20})$alkyl chain optionally substituted with one or more halo, cyano, nitro, carboxy, trifluoromethyl, trifluoromethoxy, $NH_2$, or $S(O)_2NH_2$;

$R_{10}$ is H or methyl;

or a salt thereof.

Also provided are compounds of Formula II wherein:
Y is —$(CH_2)_m$— or —$(CH_2)_mCH(CH_3)$—;
n is an integer from 1 to 2;
each $R_3$, $R_4$, $R_5$, and $R_6$ is independently OH, or $(C_1-C_6)$alkoxy;

$R_8$ is a saturated or unsaturated $(C_1-C_{20})$alkyl chain that optionally comprises one or more aryl or heteroaryl rings in the chain wherein $(C_5-C_{20})$alkyl is optionally substituted with one or more halo, cyano, nitro, carboxy, trifluoromethyl, trifluoromethoxy, $NH_2$, or $S(O)_2NH_2$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NH_2$, or $S(O)_2NH_2$;

$R_9$ is H or a saturated or unsaturated $(C_1-C_{20})$alkyl chain optionally substituted with one or more halo, cyano, nitro, carboxy, trifluoromethyl, trifluoromethoxy, $NH_2$, or $S(O)_2NH_2$;

$R_{10}$ is H or methyl;

or a salt thereof.

Also provided are compounds according to any of the above embodiments wherein herein any aryl is phenyl and any heteroaryl comprises 5-6 ring atoms of which between 1 and 4 are heteroatoms chosen from N, O, and S, either of which may be optionally substituted with one or two $(C_1-C_6)$alkyl, $(C_1-C_6)$alkoxy, halo, trifluoromethyl, or trifluoromethoxy.

Also provided are compounds according to any of the above embodiments wherein Y is —$(CH_2)_n$—. In further embodiments, n is 1. In further embodiments, n is 2.

Also provided are compounds according to any of the above embodiments wherein Y is —$(CH_2)_nCH(CH_3)$—; In further embodiments, n is 1. In further embodiments, n is 2.

A specific value for $R_1$ in Formulas I, II, Ia, and IIa and the relevant embodiments above is an unsaturated $(C_5-C_{20})$ alkyl chain.

Another value for $R_1$ is a saturated or unsaturated $(C_5-C_{20})$alkyl chain that comprises one or more aryl rings in the chain.

Another value for $R_1$ is a unsaturated $(C_5-C_{20})$alkyl chain that comprises an aryl ring in the chain.

Another value for $R_1$ is a saturated or unsaturated $(C_5-C_{20})$alkyl chain that comprises one or more heteroaryl rings in the chain.

Another value for $R_1$ is a unsaturated $(C_5-C_{20})$alkyl chain that comprises a heteroaryl ring in the chain.

A specific group of compounds of formula I and formula II are compounds wherein $R_3$, $R_4$, $R_5$ and $R_6$ are each OH.

The invention provides novel compounds disclosed herein. For example, the invention provides novel compounds of formula I and formula II wherein $R_1$ is a saturated or unsaturated $(C_5-C_{20})$alkyl chain that comprises one or more heteroaryl rings and optionally comprises one or more aryl rings in the chain wherein $(C_5-C_{20})$alkyl is optionally substituted with one or more halo, cyano, nitro, carboxy, trifluoromethyl, trifluoromethoxy, $NR_mR_n$, or $S(O)_2NR_pR_q$ and wherein any aryl or heteroaryl is optionally substituted with one or more $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$.

The invention also provides novel compounds of formula I and formula II wherein $R_1$ is —$(C_5-C_{20})$alkyl-$Z^1$ wherein $(C_5-C_{20})$alkyl is saturated or unsaturated and is optionally substituted with one or more halo, cyano, nitro, carboxy, trifluoromethyl, trifluoromethoxy, $NR_mR_n$, or $S(O)_2NR_pR_q$; and wherein $Z^1$ is heteroaryl optionally substituted with one or more (e.g. 1, 2, 3 or 4) $(C_1-C_6)$alkyl, $(C_1-C_6)$alkoxy, $(C_1-C_6)$alkanoyl, $(C_1-C_6)$alkanoyloxy, $(C_1-C_6)$alkoxycarbonyl, halo, cyano, nitro, carboxy, trifluoromethyl, trifluoromethoxy, $NR_aR_b$, or $S(O)_2NR_cR_d$.

A specific value for $Z^1$ is furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Another specific value for $Z^1$ is furyl, imidazolyl, triazolyl, triazinyl, oxazoyl, isoxazoyl, thiazolyl, isothiazoyl, pyrazolyl, pyrrolyl, pyrazinyl, tetrazolyl, thienyl, pyrimidinyl (or its N-oxide), indolyl, isoquinolyl (or its N-oxide) or quinolyl (or its N-oxide).

Another specific value for $Z^1$ is furyl, triazolyl, triazinyl, oxazoyl, isoxazoyl, thiazolyl, isothiazoyl, pyrazolyl, pyrrolyl, pyrazinyl, tetrazolyl, thienyl, pyrimidinyl (or its N-oxide), indolyl, isoquinolyl (or its N-oxide) or quinolyl (or its N-oxide).

Another specific value for $Z^1$ is indolyl.

Any of the above embodiments should also be understood to be applicable to Formulas Ia and II as appropriate, in which X is —$(CH_2)_m$—, Y is —$(CH_2)_n$—, and n and m are each 1.

Also provided is a pharmaceutical composition comprising a compound as described in any one of the above embodiments, and a pharmaceutically acceptable carrier.

Also provided is a method for inhibiting geranylgeranyl pyrophosphate synthase comprising contacting the geranylgeranyl pyrophosphate synthase in vitro or in vivo with an effective inhibitory amount of a compound as described in any one of the above embodiments. In certain embodiments, the compound is at least 2-fold selective for inhibiting geranylgeranyl pyrophosphate synthase compared to farnesylpyrophosphate synthase or squalene synthase. In further embodiments, the compound is at least 2-fold selective for inhibiting geranylgeranyl pyrophosphate synthase compared to farnesylpyrophosphate synthase and squalene synthase. In further embodiments, the compound is at least 10-fold selective for inhibiting geranylgeranyl pyrophosphate synthase compared to farnesylpyrophosphate synthase or squalene synthase. In further embodiments, the compound is at least 10-fold selective for inhibiting geranylgeranyl pyrophosphate synthase compared to farnesylpyrophosphate synthase and squalene synthase. In further embodiments, the compound is at least 100-fold selective for inhibiting geranylgeranyl pyrophosphate synthase compared to farnesylpyrophosphate synthase or squalene synthase. In further embodiments, the compound is at least 100-fold selective for inhibiting geranylgeranyl pyrophosphate synthase compared to farnesylpyrophosphate synthase and squalene synthase.

Also provided is a method for treating cancer comprising administering to an animal in need of such treatment an effective amount of a compound as described in any one of the above embodiments.

Also provided is a method for modulating testicular function comprising administering to an animal in need of such treatment an effective amount of a compound as described in any one of the above embodiments.

Also provided is a method for modulating fertility comprising administering to an animal in need of such treatment an effective amount of a compound as described in any one of the above embodiments.

Also provided is a method for treating insulin resistance comprising administering to an animal in need of such treatment an effective amount of a compound as described in any one of the above embodiments.

Also provided is a method for treating obesity comprising administering to an animal in need of such treatment an effective amount of a compound as described in any one of the above embodiments.

Also provided is a method for modulating weight gain comprising administering to an animal in need of such treatment an effective amount of a compound as described in any one of the above embodiments.

Also provided is a method for modulating osteoclast function comprising administering to an animal in need of such treatment an effective amount of a compound as described in any one of the above embodiments.

Also provided is a method for treating a parasitic infection comprising administering to an animal in need of such treatment an effective amount of a compound as described in any one of the above embodiments.

Also provided is a method for producing an antiparasitic effect comprising contacting a parasite in vitro or in vivo with an effective amount of a compound as described in any one of the above embodiments.

Also provided is a method for treating cardiac arrhythmia comprising administering to an animal in need of such treatment an effective amount of a compound as described in any one of the above embodiments.

Also provided is a compound as described in any one of the above embodiments for use in medical treatment or diagnosis.

Also provided is the use of a compound as described in any one of the above embodiments to prepare a medicament useful for treating cancer in an animal.

Also provided is the use of a compound as described in any one of the above embodiments to prepare a medicament useful for modulating testicular function in an animal.

Also provided is the use of a compound as described in any one of the above embodiments to prepare a medicament useful for modulating fertility in an animal.

Also provided is the use of a compound as described in any one of the above embodiments to prepare a medicament useful for treating insulin resistance in an animal.

Also provided is the use of a compound as described in any one of the above embodiments to prepare a medicament useful for treating obesity in an animal.

Also provided is the use of a compound as described in any one of the above embodiments to prepare a medicament useful for modulating weight gain in an animal.

Also provided is the use of a compound as described in any one of the above embodiments to prepare a medicament useful for modulating osteoclast function in an animal.

Also provided is the use of a compound as described in any one of the above embodiments to prepare a medicament useful for treating a parasitic infection in an animal.

Also provided is the use of a compound as described in any one of the above embodiments to prepare a medicament useful for treating cardiac arrhythmia in an animal.

Also provided is a compound as described in any one of the above embodiments for the prophylactic or therapeutic treatment of cancer.

Also provided is a compound as described in any one of the above embodiments for modulating testicular function.

Also provided is a compound as described in any one of the above embodiments for modulating fertility.

Also provided is a compound as described in any one of the above embodiments for the prophylactic or therapeutic treatment of treating insulin resistance.

Also provided is a compound as described in any one of the above embodiments for the prophylactic or therapeutic treatment of obesity.

Also provided is a compound as described in any one of the above embodiments for the prophylactic or therapeutic treatment of weight gain.

Also provided is a compound as described in any one of the above embodiments for modulating osteoclast function.

Also provided is a compound as described in any one of the above embodiments for the prophylactic or therapeutic treatment of a parasitic infection.

Also provided is a compound as described in any one of the above embodiments for the prophylactic or therapeutic treatment of cardiac arrhythmia.

Also provided is a compound of the invention that includes or that is linked to one or more detectable groups. In some embodiments of the invention, at least one of the one or more detectable groups is a fluorescent group. In some embodiments of the invention, at least one of the one or more detectable groups is a radionuclide.

The invention also provides a pharmaceutical composition comprising a compound of the invention and a pharmaceutically acceptable diluent or carrier.

The invention also provides a method for inhibiting geranylgeranyl pyrophosphate synthase comprising contacting the geranylgeranyl pyrophosphate synthase in vitro or in vivo with an effective inhibitory amount of a compound of the invention.

The invention also provides a method for treating cancer comprising administering to an animal (e.g. a mammal such as a human) in need of such treatment an effective amount of a compound of the invention.

The invention also provides a method for modulating (e.g., increasing or decreasing) testicular function comprising administering to an animal (e.g. a mammal such as a human) in need of such treatment an effective amount of a compound of the invention.

The invention also provides a method for modulating (e.g., increasing or decreasing) fertility comprising administering to an animal (e.g. a mammal such as a human) in need of such treatment an effective amount of a compound of the invention.

The invention also provides a method for treating insulin resistance comprising administering to an animal (e.g. a mammal such as a human) in need of such treatment an effective amount of a compound of the invention.

The invention also provides a method for treating obesity comprising administering to an animal (e.g. a mammal such as a human) in need of such treatment an effective amount of a compound of the invention.

The invention also provides a method for modulating (e.g., increasing or decreasing) weight gain comprising administering to an animal (e.g. a mammal such as a human) in need of such treatment an effective amount of a compound of the invention.

The invention also provides a method for modulating (e.g., increasing or decreasing) osteoclast function comprising administering to an animal (e.g. a mammal such as a human) in need of such treatment an effective amount of a compound of the invention.

The invention also provides a method for treating a parasitic infection comprising administering to an animal (e.g. a mammal such as a human) in need of such treatment an effective amount of a compound of the invention.

The invention also provides a method for producing an antiparasitic effect comprising contacting a parasite in vitro or in vivo with an effective amount of a compound of the invention.

The invention also provides a compound of the invention for use in medical treatment or diagnosis.

The invention also provides a method for imaging a tissue including contacting the tissue with an effective amount of a compound of the invention and detecting the compound so as to image the tissue.

The invention also provides a method for treating cardiac arrhythmia including administering to an animal (e.g. a mammal such as a human) in need of such treatment an effective amount of a compound of the invention.

The invention also provides the use of a compound of the invention to prepare a medicament useful for treating cardiac arrhythmia in an animal (e.g. a mammal such as a human).

The invention also provides the use of a compound a compound of the invention to prepare a medicament useful for treating cancer in an animal (e.g. a mammal such as a human).

The invention also provides the use of a compound of the invention to prepare a medicament useful for modulating (e.g., increasing or decreasing) testicular function in an animal (e.g. a mammal such as a human).

The invention also provides the use of a compound a compound of the invention to prepare a medicament useful for modulating (e.g., increasing or decreasing) fertility in an animal (e.g. a mammal such as a human).

The invention also provides the use of a compound a compound of the invention to prepare a medicament useful for treating insulin resistance in an animal (e.g. a mammal such as a human).

The invention also provides the use of a compound of the invention to prepare a medicament useful for treating obesity in an animal (e.g. a mammal such as a human).

The invention also provides the use of a compound of the invention to prepare a medicament useful for modulating (e.g., increasing or decreasing) weight gain in an animal (e.g. a mammal such as a human).

The invention also provides the use of a compound of the invention to prepare a medicament useful for modulating (e.g., increasing or decreasing) osteoclast function in an animal (e.g. a mammal such as a human).

The invention also provides the use of a compound of the invention to prepare a medicament useful for treating a parasitic infection in an animal (e.g. a mammal such as a human).

The invention also provides a compound of the invention for the prophylactic or therapeutic treatment of cancer.

The invention also provides a compound of the invention for modulating testicular function.

The invention also provides a compound of the invention for modulating fertility.

The invention also provides a compound of the invention for the prophylactic or therapeutic treatment of treating insulin resistance.

The invention also provides a compound of the invention for the prophylactic or therapeutic treatment of obesity.

The invention also provides a compound of the invention for the prophylactic or therapeutic treatment of weight gain.

The invention also provides a compound of the invention for modulating osteoclast function.

The invention also provides a compound of the invention for the prophylactic or therapeutic treatment of a parasitic infection.

The invention also provides a compound of the invention for the prophylactic or therapeutic treatment of cardiac arrhythmia.

The invention also provides processes and intermediates disclosed herein that are useful for preparing compounds of formula I and formula II, or salts thereof. For example, the invention provides compounds of formula 101 and 102:

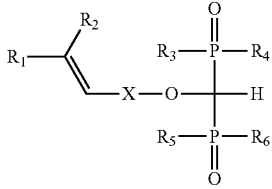

101

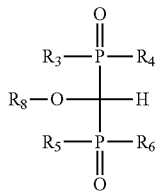

102 wherein $R_1$-$R_6$ and $R_8$ have any of the values defined herein, which are useful as intermediates for preparing the corresponding compounds of formula I and II, or the salts thereof. In one aspect the invention provides a compound of formula 102 wherein $R_8$ is a saturated or unsaturated $(C_1$-$C_{20})$alkyl chain. In another aspect the invention provides a compound of formula 102 wherein $R_8$ is a saturated or unsaturated $(C_5$-$C_{20})$alkyl chain. In another aspect the invention provides a compound of formula 102 wherein $R_8$ is:

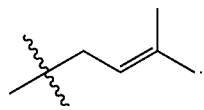 [SMILES: *CC=C(C)C]

In another aspect the invention provides a compound of formula 102 wherein $R_8$ is:

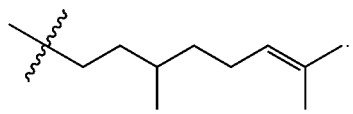 [SMILES: *CCC(C)CCC=C(C)C]

In another aspect the invention provides a compound of formula 102 wherein $R_8$ is:

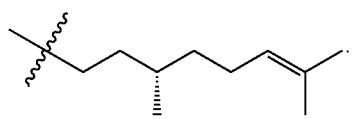 [SMILES: *CC[C@@H](C)CCC=C(C)C]

Certain compounds of formula 101 and 102 may also have useful GGPP synthase inhibiting activity or squalene synthase inhibiting activity.

The following definitions are used, unless otherwise described: halo is fluoro, chloro, bromo, or iodo. Alkyl (and the equivalent term, "alkyl chain"), alkoxy, etc. denote both straight and branched groups; but reference to an individual radical such as propyl embraces only the straight chain radical, a branched chain isomer such as isopropyl being specifically referred to. Unsaturated $(C_1$-$C_{20})$alkyl denotes a $(C_2$-$C_{20})$alkyl with at least one unsaturated (i.e. double or triple) bond. Unsaturated $(C_5$-$C_{20})$alkyl denotes a $(C_5$-$C_{20})$ alkyl with at least one unsaturated (i.e. double or triple) bond. Aryl denotes a phenyl radical or an ortho-fused bicyclic carbocyclic radical having about nine to ten ring atoms in which at least one ring is aromatic. Heteroaryl encompasses a radical of a monocyclic aromatic ring containing five or six ring atoms consisting of carbon and one to four heteroatoms each selected from the group consisting of non-peroxide oxygen, sulfur, and N(X) wherein X is absent or is H, O, $(C_1$-$C_4)$alkyl, phenyl or benzyl, as well as a radical of an ortho-fused bicyclic heterocycle of about eight to ten ring atoms comprising one to four heteroatoms each selected from the group consisting of non-peroxide oxygen, sulfur, and N(X).

As used herein, a saturated or unsaturated $(C_1$-$C_{20})$alkyl chain that comprises one or more aryl or heteroaryl rings in the chain, and a saturated or unsaturated $(C_5$-$C_{20})$alkyl chain that comprises one or more aryl or heteroaryl rings in the chain, each include: 1) alkyl chains that have an aryl or heteroaryl within the chain so as to have one portion of the alkyl chain attached to one atom of the aryl or heteroaryl and another portion of the alkyl chain attached to a different atom of the aryl or heteroaryl and 2) alkyl chains that are terminated with an aryl or heteroaryl.

In one embodiment of the invention, the saturated or unsaturated $(C_5$-$C_{20})$alkyl chain that comprises one or more aryl or heteroaryl rings in the chain of $R_1$, includes the aryl or heteroaryl within the chain so as to have one portion of the alkyl chain attached to one atom of the aryl or heteroaryl and another portion of the alkyl chain attached to a different atom of the aryl or heteroaryl.

The term "prodrug" is well understood in the art and includes compounds that are converted to pharmaceutically active compounds in vivo (e.g. in an animal such as a mammal). For example, see *Remington's Pharmaceutical Sciences,* 1980, vol. 16, Mack Publishing Company, Easton, Pa., 61 and 424. In particular, a number of groups suitable for preparing prodrug forms of phosphorous containing compounds (e.g. phosphonates) are known. For example, see Galmarini C M, et al., *International Journal of Cancer,* 2003, 107 (1), 149-154; Wagner, C. R., et al., *Medicinal Research Reviews,* 2000, 20, 417-51; McGuigan, C., et al., *Antiviral Research,* 1992, 17, 311-321; and Chapman, H., et al., *Nucleosides, Nucleotides & Nucleic Acids,* 2001, 20, 1085-1090. The invention includes phosphonate prodrug analogs prepared from suitable in vivo hydrolysable groups. In one specific embodiment the invention provides for phosphonate prodrugs of the compounds of formula I and formula II wherein the phosphonate is pivaloyloxymethyl (i.e. wherein one or more of $R_3$, $R_4$, $R_5$ or $R_6$ is —OCH$_2$OC(O)C(CH$_3$)$_3$).

It will be appreciated by those skilled in the art that compounds of the invention having a chiral center may exist in and be isolated in optically active and racemic forms. For example, it is possible for one or both phosphorous atoms in a compound of formula I or formula II to be chiral centers. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine enzyme inhibitory activity using the standard tests that are well known in the art.

Specific and preferred values listed below for radicals, substituents, and ranges, are for illustration only; they do not exclude other defined values or other values within defined ranges for the radicals and substituents.

Specifically, $(C_1-C_6)$alkyl can be methyl, ethyl, propyl, isopropyl, butyl, iso-butyl, secbutyl, pentyl, 3-pentyl, or hexyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkanoyloxy can be formyloxy, acetoxy, propanoyloxy, butanoyloxy, isobutanoyloxy, pentanoyloxy, or hexanoyloxy; and aryl can be phenyl, indenyl, or naphthyl; and heteroaryl can be furyl, imidazolyl, triazolyl, triazinyl, oxazoyl, isoxazoyl, thiazolyl, isothiazolyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

Representative compounds of the invention can be prepared as illustrated in Scheme 1.

Scheme 1. General preparation of compounds.

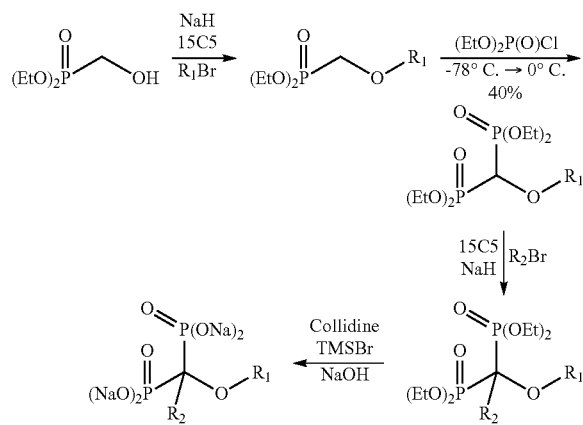

In Scheme I above, $R_1$ and $R_2$ represent groups linked through a carbon atom, and are not to be limited by the definitions of $R_1$ and $R_2$ set forth elsewhere in this specification.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I and formula II can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I and formula II to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Certain embodiments of the present invention provide compounds that act as GGPP synthase inhibitors. While not intended to be a limitation of the present invention, the ability of compounds of the invention to inhibit GGPP synthase will enable the art worker to use these compounds to affect certain processes that are influenced by GGPP synthase. For example, certain embodiments of the present invention provide methods for treating cancer, modulating (e.g., increasing or decreasing) testicular function, modulating (e.g., increasing or decreasing) fertility, treating insulin resistance, treating obesity, modulating (e.g., increasing or decreasing) weight gain, modulating (e.g., increasing or decreasing) osteoclast function, treating a parasitic infection, producing an antiparasitic effect, and for treating cardiac arrhythmia. Certain embodiments of the present invention also provide the use of a compound of the invention to prepare a medicament useful for treating cancer, modulating (e.g., increasing or decreasing) testicular function, modulating (e.g., increasing or decreasing) fertility, treating insulin resistance, treating obesity, modulating (e.g., increasing or decreasing) weight gain, modulating (e.g., increasing or decreasing) osteoclast function, treating a parasitic infection, and for treating cardiac arrhythmia in an animal. Compounds of the invention may also induce different cardiac rhythms, and the compounds thus might also be used to induce the different cardiac rhythms, e.g., reversible asystole, e.g., during a cardiac bypass procedure and to prepare useful medicaments useful for the same. The ability of a compound of the invention to cause these effects can be evaluated by the art worker using assays known in the art.

The invention also provides a detectable compound that is a compound of formula I or formula II that includes or that is linked to one or more detectable groups. Detectable groups include, but are not limited to, fluorescent groups and radionuclides. For example, a detectable compound that includes a fluorescent group is exemplified in Example 7. Such compounds are useful, e.g., as probes, e.g., for identifying tissues that include geranylgeranyl pyrophosphate synthase or for elucidating geranylgeranyl pyrophosphate synthase function. The invention also provides tissue including a compound of the invention bound to geranylgeranyl pyrophosphate synthase.

Detectable compounds of the invention, e.g., radiolabeled compounds of formula I and formula II, are useful as imaging agents for imaging cells and tissues that include geranylgeranyl pyrophosphate synthase. Accordingly, the invention also provides compounds of formula I and formula II that include or that are linked to one or more detectable radionuclides (e.g., one or more metallic radionuclide and/or one or more non-metallic radionuclides). For example, a detectable radionuclide can be incorporated into a compound by replacing an atom of the compound of formula I or formula II with a radionuclide (e.g., non-metallic radionuclide). Alternatively, a radiolabeled compound of the invention can be prepared by linking a compound of formula I or formula II to a chelating group that includes a detectable radionuclide (e.g., metallic radionuclide). Methods for making such detectable compounds are known to the art worker. Such compounds can be useful to image tissues with geranylgeranyl pyrophosphate synthase activity in vivo or in vitro.

As used herein, a "chelating group" is a group that can include a detectable group, e.g., a radionuclide (e.g., a metallic radioisotope). Any suitable chelating group can be employed. Suitable chelating groups are disclosed, e.g., in Poster Sessions, Proceedings of the 46th Annual Meeting, J. Nuc. Med., p. 316, No. 1386; Scientific Papers, Proceedings of the 46th Annual Meeting, J. Nuc. Med., p. 123, No. 499; Scientific Papers, Proceedings of the 46th Annual Meeting, J. Nuc. Med., p. 102, No. 413; Scientific Papers, Proceedings of the 46th Annual Meeting, J. Nuc. Med., p. 102, No. 414; Scientific Papers, Proceedings of the 46th Annual Meeting, J. Nuc. Med., p. 103, No. 415; Poster Sessions, Proceedings of the 46th Annual Meeting, J. Nuc. Med., p. 318, No. 1396; Poster Sessions, Proceedings of the 46th Annual Meeting, J. Nuc. Med., p. 319, No. 1398; M. Moi et al., J. Amer. Chem., Soc., 49, 2639 (1989); S. V. Deshpande et al., J. Nucl. Med., 31, 473 (1990); G. Kuser et al., Bioconj. Chem., 1, 345 (1990); C. J. Broan et al., J. C. S. Chem. Comm., 23, 1739 (1990); C. J. Anderson et al., J. Nucl. Med. 36, 850 (1995); U.S. Pat. No. 5,739,313; and U.S. Pat. No. 6,004,533.

As used herein, a "detectable radionuclide" is any suitable radionuclide (i.e., a radioisotope) useful in an imaging procedure, e.g., a diagnostic procedure, in vivo or in vitro. Suitable detectable radionuclides include metallic radionuclides (i.e., metallic radioisotopes) and non-metallic radionuclides (i.e., non-metallic radioisotopes).

Suitable metallic radionuclides (i.e., metallic radioisotopes or metallic paramagnetic ions) include Antimony-124, Antimony-125, Arsenic-74, Barium-103, Barium-140, Beryllium-7, Bismuth-206, Bismuth-207, Cadmium-109, Cadmium-115m, Calcium-45, Cerium-139, Cerium-141, Cerium-144, Cesium-137, Chromium-51, Cobalt-55, Cobalt-56, Cobalt-57, Cobalt-58, Cobalt-60, Cobalt-64, Copper-67, Erbium-169, Europium-152, Gallium-64, Gallium-68, Gadolinium-153, Gadolinium-157 Gold-195, Gold-199, Hafnium-175, Hafnium-175-181, Holmium-166, Indium-110, Indium-111, Iridium-192, Iron-55, Iron-59, Krypton-85, Lead-210, Manganese-54, Mercury-197, Mercury-203, Molybdenum-99, Neodymium-147, Neptunium-237, Nickel-63, Niobium-95, Osmium-185+191, Palladium-103, Platinum-195m, Praseodymium-143, Promethium-147, Protactinium-233, Radium-226, Rhenium-186, Rhenium-188, Rubidium-86, Ruthenium-103, Ruthenium-106, Scandium-44, Scandium-46, Selenium-75, Silver-110m, Silver-111, Sodium-22, Strontium-85, Strontium-89, Strontium-90, Sulfur-35, Tantalum-182, Technetium-99m, Tellurium-125, Tellurium-132, Thallium-204, Thorium-228, Thorium-232, Thallium-170, Tin-113, Tin-114, Tin-117m, Titanium-44, Tungsten-185, Vanadium-48, Vanadium-49, Ytterbium-169, Yttrium-86, Yttrium-88, Yttrium-90, Yttrium-91, Zinc-65, and Zirconium-95.

In some embodiments of the invention, the chelating group can include more than one metallic radioisotope. In some embodiments, the detectable chelating group can include 2 to about 10, 2 to about 8, 2 to about 6, or 2 to about 4 metallic radioisotopes.

The non-metallic radionuclide can be a non-metallic paramagnetic atom (e.g., Fluorine-19); or a non-metallic positron emitting radionuclide (e.g., Carbon-11, Fluorine-18, Iodine-123, or Bromine-76). In some embodiments of the invention, the non-metallic radionuclide is phosphorous-32.

In some embodiments of the invention, the compounds of the present invention can include more than one non-metallic radioisotope. In some embodiments, the compounds of the present invention can include 2 to about 10, 2 to about 8, 2 to about 6, or 2 to about 4 non-metallic radioisotopes.

Test A: Biological Activity

Figure 3:
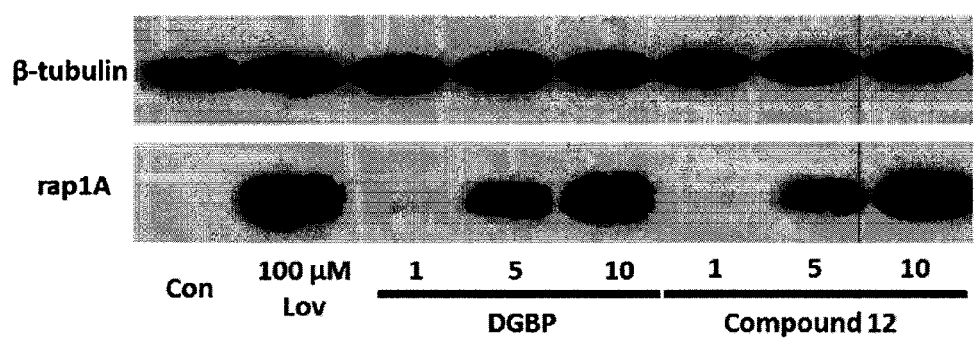
FIG. 3 shows a Western Blot illustrating a bioactivities comparison for Compound 12 and digeranyl bisphosphonate (DGBP) in a variation of Test A.
Figure 4A:
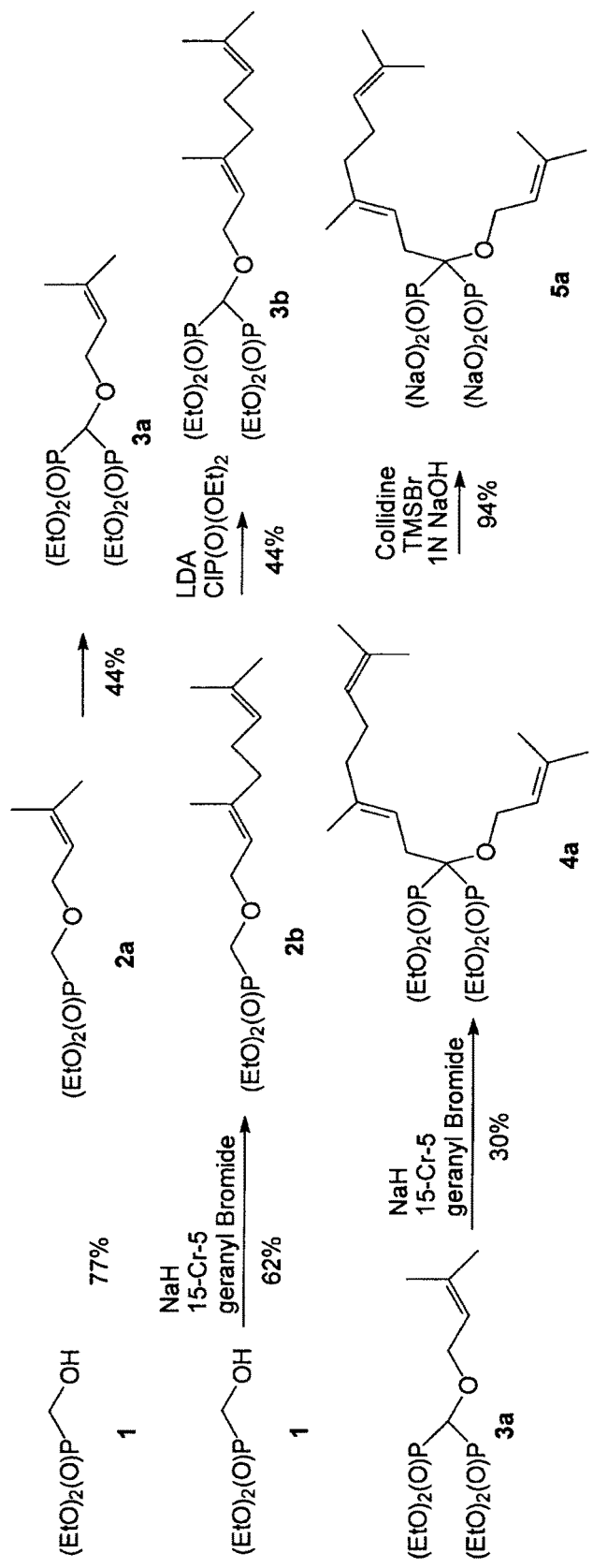
FIG. 4A-4D illustrate the synthesis of Compounds 5a-5d, 6a, 6b, 10, 12, and 14.
Figure 4B:
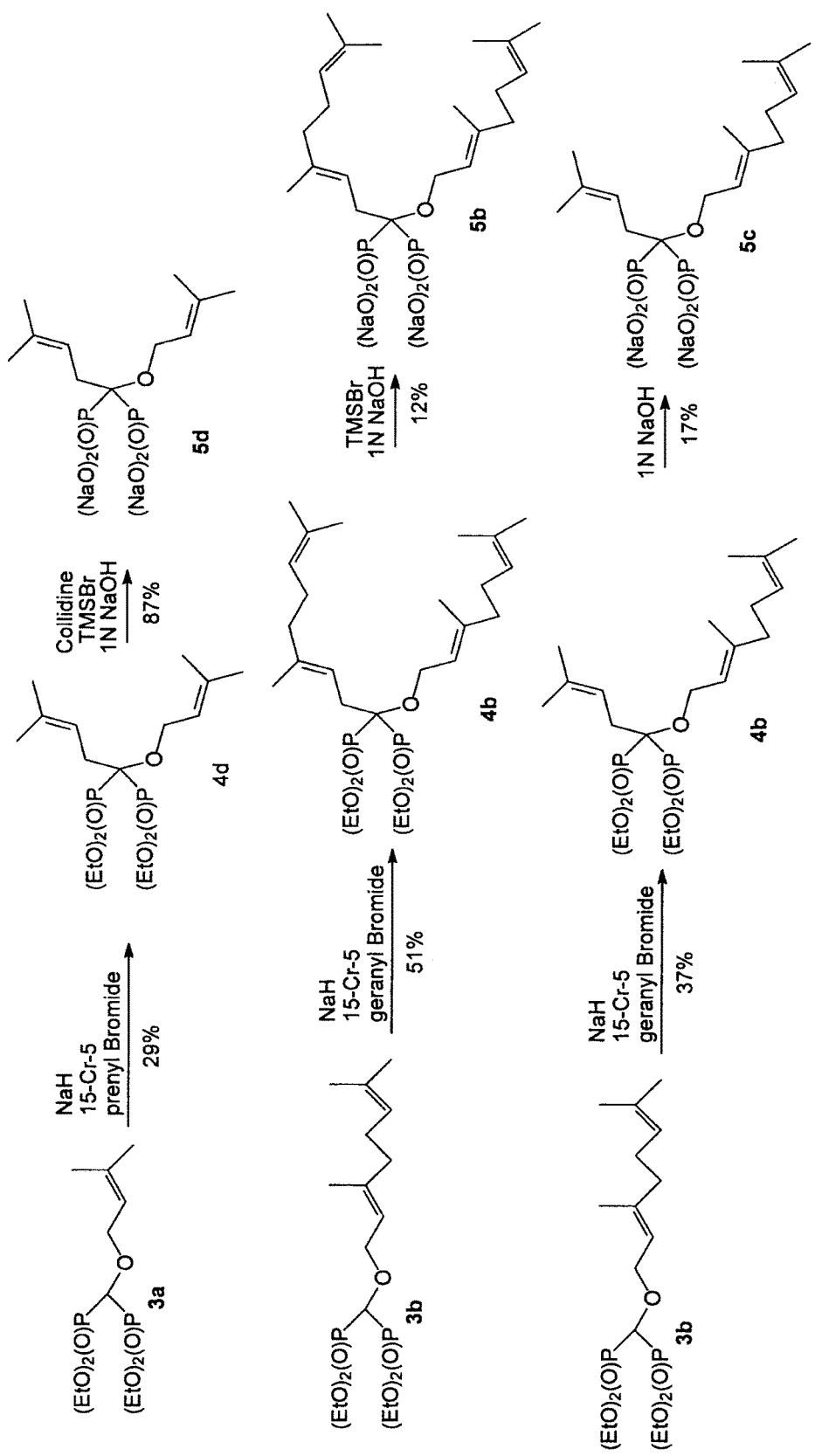
Figure 4C:
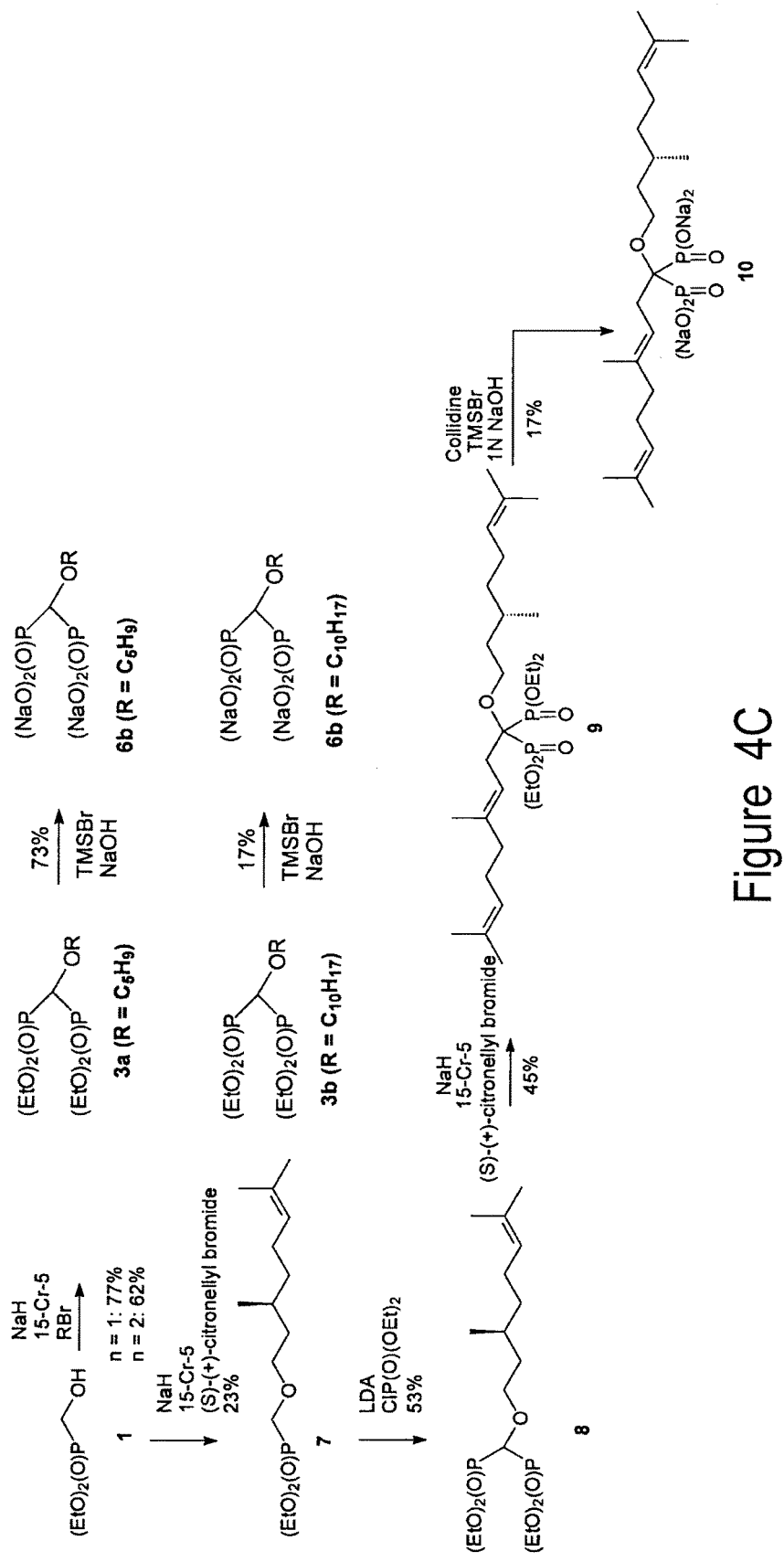
Figure 4D:
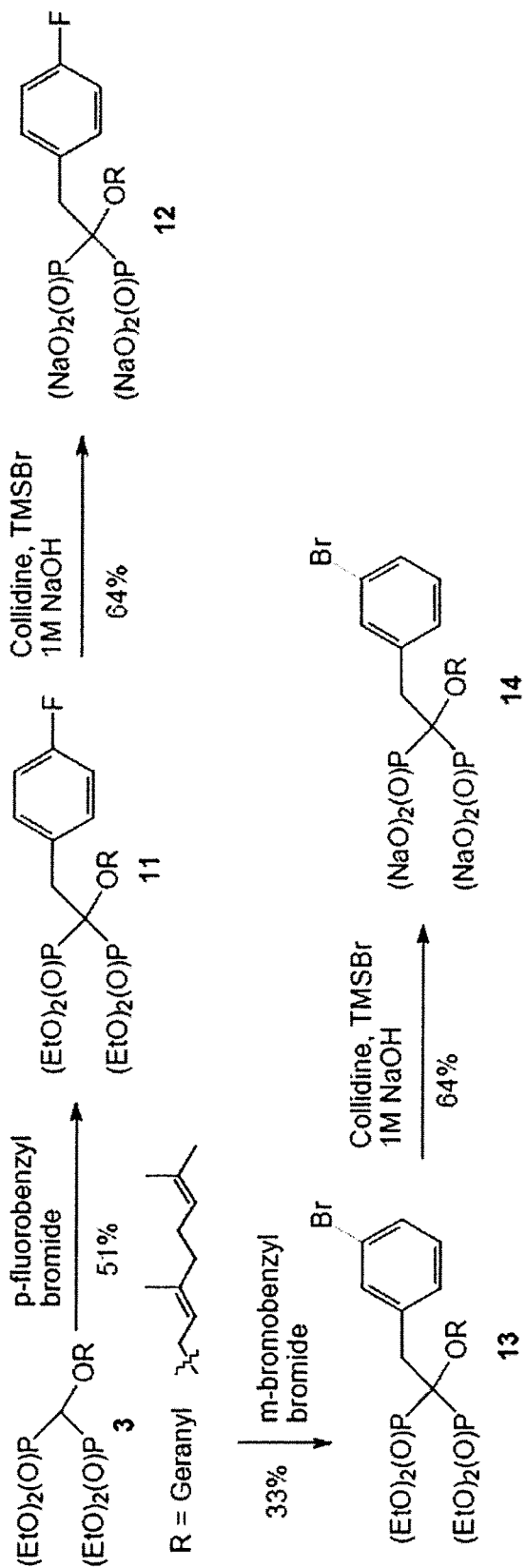

The activity of a compound can be evaluated in a Rap1A geranylgeranylation assay (for example see, Dudakovic, Wiemer et al. *J. Pharm. Exp. Therap.* 324, 2008, 1028-1036; and Wiemer, Yu et al. *Bioorg. Med. Chem.* 15, 2007, 1959-1966; and refs therein). In one protocol, K562 leukemia cells were treated for 48 h with DGBP or compound 5b, and analyzed for inhibition of Rap1a geranylgeranylation by Western blot analysis, with α-tubulin as a control. Data from this assay for the compound DGBP and for compound 5b is shown in FIG. 1. In a variation, DU145 prostate cancer cells were treated for 24 h with DGBP or compound 12, and analyzed as above, but with β-tubulin as a control. Data from this assay for the compound DGBP and compound 12 is shown in FIG. 3. Other compounds disclosed herein are expected to be active as well.

Test B: FPP and GGPP Level Determinations

Figure 2:
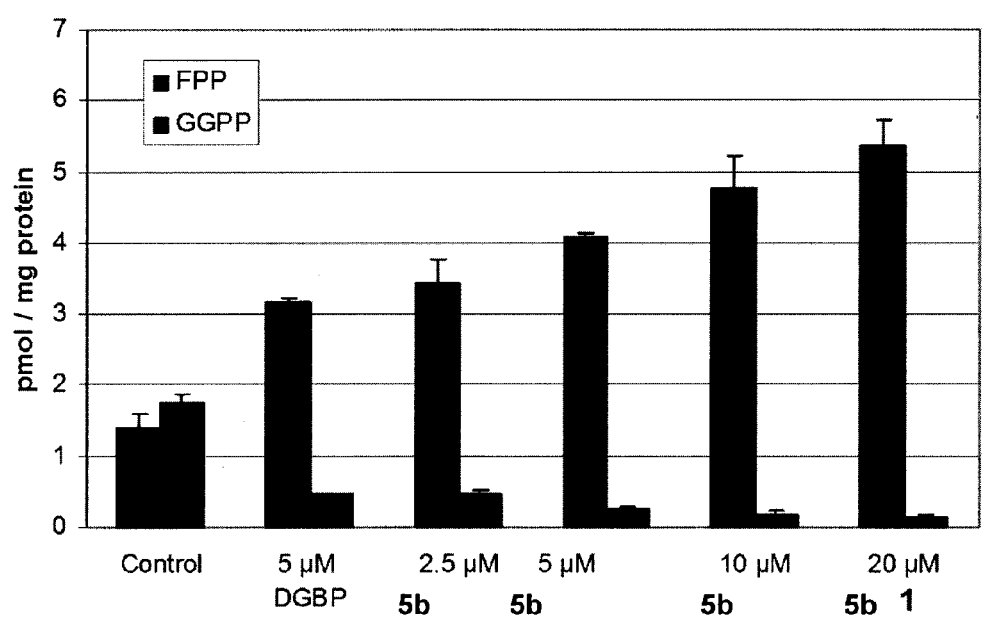
FIG. 2 illustrates cellular FPP and GGPP levels measured in vitro for Compound 5b in Test B. In this assay, GPP was reduced by increasing concentration of 5b, whereas FPP was not.

FPP and GGPP levels can be determined using the assay reported by Tong H, Holstein S A, and Hohl R J. *Anal Biochem.* 2005 Jan. 1; 336(1):51-9. Data for compound 5b in this assay, run for 48 hours in K562 cells, is presented in FIG. 2. Other compounds disclosed herein are expected to be active as well.

Test C: Inhibition of GGPP Synthase of Mammalian Origin.

FPP or GGPP synthase activity may be measured by the method of Reed and Rilling (Reed, B. C. & Rilling, H. C. (1976) *Biochemistry* 15, 3739-3745) with modifications. In one protocol, assays are set up such that the final volume was 100 ul. The assay conditions may be 50 mM Tris pH7.7, 2 mM $MgCl_2$, 0.5 mM TCEP, 20 µg/ml BSA. For FPP synthase assays the final enzyme concentration are 10 nM and for GGPP synthase assays the final enzyme concentration are 20 nM. All substrates are at 10 µM final concentration each substrate, all reactions were with IPP (14C-IPP, 400 KBq/µMol American Radiochem. Corp). For FPP synthase, GPP is the second substrate, and for GGPP synthase FPP is the second substrate. Bisphosphonate is added as $\frac{1}{10}^{th}$ volume of a 10× stock solution and allowed to preincubate for 10 minutes with the enzyme in a volume of 80 ul and the reaction started by the addition of 20 ul of the combined substrate. The reaction is allowed to proceed for 4 minutes at 37° C. before being terminated by the addition of 0.2 ml of conc. HCl/Methanol (1:4) and incubated for a further 10 mins at 37° C. The reaction mixtures are then extracted with 0.4 ml of immiscible scintillation fluid (Microscint E, Perkin Elmer) to separate reaction products from unused substrate and are counted directly with a microbeta scintillation counter (Perkin Elmer). Data may be analysed using Graphpad Prism. It is expected that bisphosphonates disclosed herein will inhibit GGPP synthase.

The above methods may also be performed as disclosed in A. J. Wiemer et al., "Digeranyl bisphosphonate inhibits geranylgeranyl pyrophosphate synthase," *Biochem Biophys Res Comm*, 353 (2007) 921-925.

The invention will now be illustrated by the following non-limiting Examples.

EXAMPLES

General

Compounds were identified using $^1$H NMR, $^{13}$C NMR, $^{31}$P NMR or comparison to authentic sample where applicable. Glassware was flame-dried prior to use. Reactions were carried out with stirring under a positive argon atmosphere unless otherwise indicated. All NMR data were collected at 300 MHz in $CDCl_3$ unless otherwise noted.

Experimental

Monophosphonate Ether 2b (n=2) (Known Compound).

Diethyl hydroxymethylphosphonate (1 mL, 6.8 mmol) was added dropwise to a solution of NaH (300 mg, 7.5 mmol) in THF (7 mL) in an ice bath, followed by addition of 15-crown-5 as a solution in THF (1 M, 0.1 mL). After 30 minutes, geranyl bromide (1.62 g, 7.5 mmol) was added to the reaction mixture and it was allowed to react at room temperature overnight. Once the reaction was complete based on analysis of the $^{31}$P NMR spectrum, saturated NH$_4$Cl was added. The resulting residue was extracted with Et$_2$O, the organic extracts were combined, dried (Na$_2$SO$_4$), concentrated in vacuo, and purified by column chromatography (5% EtOH in hexane) to afford the desired product 2 as a colorless oil (1.27 g, 62%): $^1$H NMR (300 MHz, CDCl$_3$) δ 5.31 (t, J=6.5 Hz, 1H), 5.08 (t, J=4.9 Hz, 1H), 4.25-4.09 (m, 6H), 3.74 (d, J$_{HP}$=8.6 Hz, 2H), 2.17-1.98 (m, 4H), 1.68 (s, 6H) 1.60 (s, 3H), 1.35 (t, J=7.3 Hz, 6H); $^{13}$C NMR (75 MHz, CDCl$_3$) δ 141.7, 131.5, 123.6, 119.6, 69.0 (d, J$_{CP}$=12.7 Hz), 62.9 (d, J$_{CP}$=166.0 Hz), 62.1 (d, J$_{CP}$=6.1 Hz, 2C), 39.4, 26.0, 25.5, 17.4, 16.3, 16.2 (2C); $^{31}$P NMR (121 MHz, CDCl$_3$) δ 22.0.

Bisphosphonate 3a.

A solution of n-butyl lithium in hexanes (8.8 mL, 21.2 mmol) was added to a solution of diisopropylamine (2.75 mL, 19.5 mmol) in THF (16 mL) at −78° C. and the reaction was allowed to stir for 30 minutes. Ether 2 (2 g, 8.5 mmol) was then added to the reaction mixture dropwise (over 90 minutes) and allowed to react for additional one hour then followed by the careful addition of diethyl chlorophosphate (2.9 mL, 19.5 mmol). After it was allowed to warm to room temperature slowly and to stir overnight, the reaction was quenched by the addition of water. The aqueous layer was extracted with EtOAc, and the combined organic layers were dried with Na$_2$SO$_4$ and concentrated in vacuo. The resulting residue was purified by column chromatography (5% EtOH in hexane) to afford the desired product 3 (n=1) as a colorless oil (1.39 g, 44%): $^1$H NMR (300 MHz, CDCl$_3$) δ 5.34 (t, J=7.2 Hz, 1H), 4.36-4.08 (m, 8H), 4.32 (d, J=7.1 Hz, 2H), 4.03 (t, J$_{HP}$=17.5 Hz, 1H), 1.77 (s, 3H), 1.72 (s, 3H), 1.37 (t, J=7.3 Hz, 12H); $^{13}$C NMR (75 MHz, CDCl$_3$) δ 139.1, 119.3, 70.1 (t, J$_{CP}$=156.9 Hz), 69.4 (t, J$_{CP}$=5.2 Hz), 62.9 (t, J$_{CP}$=2.6 Hz, 2C), 62.7 (t, J$_{CP}$=3.2 Hz, 2C), 25.4, 17.6, 16.1 (t, J$_{CP}$=2.9 Hz, 2C), 16.0 (t, J$_{CP}$=3.6 Hz, 2C); $^{31}$P NMR (121 MHz, CDCl$_3$) δ 16.2. HRMS (ES$^+$, m/z) calcd for (M+Na)$^+$ C$_{14}$H$_{30}$O$_7$NaP$_2$: 395.1365. found: 395.1395.

Bisphosphonate 4b.

Compound 3 (325 mg, 0.74 mmol) was added into a solution of NaH (50 mg, 1.25 mmol) in anhydrous THF (3 mL) and the reaction mixture was allowed to stir for 30 minutes. Geranyl bromide (300 mg, 1.38 mmol) was then added to allow stirring at room temperature overnight. Reaction progress was monitored by the analysis of $^{31}$P NMR spectrum. Once it complete, water was added to quench the reaction. The resulting residue was then extracted with EtOAc and washed with brine. The remaining organic layer was dried (Na$_2$SO$_4$) and concentrated in vacuo, and the residue was purified by column chromatography (5% EtOH in Hexane) to afford compound 4b as a colorless oil (220 mg, 51%): $^1$H NMR (300 MHz, CDCl$_3$) δ 5.50 (t, J=6.7 Hz, 1H), 5.34 (t, J=5.6 Hz, 1H), 5.16-5.05 (m, 2H), 4.37 (d, J=6.8 Hz, 2H), 4.30-4.17 (m, 8H), 2.98-2.82 (m, 2H), 2.16-1.98 (m, 8H), 1.68 (s, 12H), 1.61 (s, 6H), 1.35 (t, J=6.9 Hz, 6H), 1.35 (t, J=6.9 Hz, 6H); $^{13}$C NMR (75 MHz, CDCl$_3$) δ 139.6, 136.7, 131.4, 131.2, 124.3, 123.9, 120.8, 117.8 (t, J$_{CP}$=7.9 Hz), 80.7 (t, J$_{CP}$=151.0 Hz), 63.2 (t, J$_{CP}$=3.6 Hz 3C), 62.9 (t, J$_{CP}$=3.7 Hz, 2C), 40.0, 39.5, 30.0, 26.6, 26.3, 25.6 (2C), 17.6 (2C), 16.5 (t, J$_{CP}$=3.0 Hz, 2C), 16.4 (t, J$_{CP}$=2.5 Hz, 2C), 16.4, 16.3; $^{31}$P NMR (121 MHz, CDCl$_3$) δ 19.0. HRMS (ES$^+$, m/z) calcd for (M+Na)$^+$ C$_{29}$H$_{54}$O$_7$NaP$_2$: 599.3243; found: 599.3244.

Phosphonic Acid 5a.

The base, 2, 4, 6-collidine (0.22 mL, 1.67 mmol), was added into the ice cold solution of bisphosphonate 4a (85 mg, 0.17 mmol) in CH$_2$Cl$_2$ (5 mL) followed by the addition of excess TMSBr (0.27 mL, 2.00 mmol). The reaction was allowed to warm slowly to room temperature and allowed to stir overnight. Once the reaction was complete based on the analysis of the $^{31}$P NMR spectrum, the solution was removed under vacuo. The resulting residue was further washed with toluene and concentrated repeatedly to remove any remaining TMSBr. It was then treated with NaOH solution (0.27 mL 5M NaOH, 2 mL H$_2$O) for 10 minutes and then the water was removed on a lyophilizer to obtain the crude salt. This material was precipitated with the dry acetone to obtain the desired product, the pure salt as a white solid (77.1 mg, 94%): $^1$H NMR (500 MHz, D$_2$O) δ 5.84 (s, 1H), 5.39 (t, J=6.8 Hz, 1H), 5.22-5.17 (m, 1H), 4.17 (d, J=7.0 Hz, 2H), 2.89-2.79 (m, 2H), 2.16-2.03 (m, 4H), 1.72 (s, 3H), 1.69 (s, 3H), 1.68 (s, 3H), 1.65 (s, 3H), 1.62 (s, 3H); $^{13}$C NMR (125 MHz, D$_2$O) δ 140.6, 133.7, 131.4, 124.2, 123.1 (t, J$_{CP}$=6.4 Hz), 122.4, 82.4 (t, J$_{CP}$=134.7 Hz), 61.1 (t, J$_{CP}$=6.2 Hz), 39.1, 29.7, 25.9, 25.4, 25.0, 17.4, 17.1, 15.6; $^{31}$P NMR (201 MHz, D$_2$O) δ 17.8. HRMS (ES$^-$, m/z) calcd for (M−H)$^-$ C$_{16}$H$_{29}$O$_7$P$_2$: 395.1389. found: 395.1388.

Monophosphonate Ether 2a (n=1) (Known Compound).

Yield, 77%; colorless oil; $^1$H NMR (300 MHz, CDCl$_3$) δ 5.36-5.28 (m, 1H), 4.23-4.11 (m, 4H), 4.10 (d, J=7.1 Hz, 2H), 3.74 (d, J$_{HP}$=8.4 Hz, 2H), 1.76 (s, 3H), 1.70 (s, 3H), 1.35 (t, J=7.0 Hz, 6H); $^{13}$C NMR (75 MHz, CDCl$_3$) δ 137.8, 119.6, 68.6 (d, J$_{CP}$=12.0 Hz), 62.7 (d, J$_{CP}$=166.8 Hz), 61.7 (d, J$_{CP}$=6.1 Hz), 25.2, 17.4, 15.9 (d, J$_{CP}$=5.1 Hz); $^{31}$P NMR (121 MHz, CDCl$_3$) δ 21.7.

Bisphosphonate 3b (n=2).

Yield, 44%; colorless oil; $^1$H NMR (300 MHz, CDCl$_3$) 5.26 (t, J=7.0 Hz, 1H), 5.01 (t, J=6.7 Hz, 1H), 4.27 (t, J=7.5 Hz, 2H), 4.23-4.10 (m, 8H), 3.95 (t, J$_{HP}$=17.6 Hz, 1H), 2.09-1.93 (m, 4H), 1.63 (s, 3H), 1.63 (s, 3H), 1.60 (s, 3H), 1.28 (t, J=7.3 Hz, 12H); $^{13}$C NMR (75 MHz, CDCl$_3$) δ 142.1, 131.0, 123.2, 119.0, 70.1 (t, J$_{CP}$=157.9 Hz), 69.2 (t, J$_{CP}$=5.1 Hz), 62.7 (t, J$_{CP}$=4.1 Hz, 2C), 62.5 (t, J$_{CP}$=3.2 Hz, 2C), 39.1, 25.7, 25.0, 17.0, 15.9 (t, J$_{CP}$=2.4 Hz, 2C), 15.8 (t, J$_{CP}$=2.7 Hz, 2C), 15.8; $^{31}$P NMR (121 MHz, CDCl$_3$) δ 16.1; HRMS (ES$^+$, m/z) calcd (M+Na)$^+$ C$_{19}$H$_{38}$O$_7$P$_2$Na: 463.1991. found: 463.1972.

Bisphosphonate 4a.

Yield, 30%; colorless oil; $^1$H NMR (300 MHz, CDCl$_3$) δ 5.45 (t, J=6.9 Hz, 1H), 5.33 (t, J=6.5 Hz, 1H), 5.13-5.04 (m, 1H), 4.37 (d, J=6.5 Hz, 2H), 4.30-4.16 (m, 8H), 2.88 (td, J$_{HP}$=14.2 Hz, J=6.5 Hz, 2H), 2.15-1.97 (m, 4H), 1.73 (s, 3H), 1.68 (s, 3H), 1.66 (s, 6H), 1.61 (s, 3H), 1.35 (t, J=6.9 Hz, 6H), 1.34 (t, J=7.3 Hz, 6H); $^{13}$C NMR (75 MHz, CDCl$_3$) δ 139.7, 133.2, 131.6, 124.0, 120.8, 118.0 (t, J$_{CP}$=7.5 Hz), 80.7 (t, J$_{CP}$=150.9 Hz), 63.3 (t, J$_{CP}$=5.9 Hz), 63.3 (t, J$_{CP}$=3.2 Hz, 2C), 63.0 (t, J$_{CP}$=3.0 Hz, 2C), 39.5, 30.2, 26.4, 26.0, 25.7, 18.1, 17.7, 16.5 (t, J$_{CP}$=3.2 Hz, 4C), 16.5; $^{31}$P NMR (121 MHz, CDCl$_3$) δ 19.0.

Bisphosphonate 4c.

Yield, 37%; colorless oil; $^1$H NMR (300 MHz, CDCl$_3$) δ 5.48 (t, J=6.2 Hz, 1H), 5.31 (t, J=6.7 Hz, 1H), 5.16-5.04 (m, 1H), 4.33 (d, J=6.8 Hz, 2H), 4.30-4.10 (m, 8H), 2.89 (td, J$_{HP}$=14.5 Hz, J=6.4 Hz, 2H), 2.15-1.96 (m, 4H), 1.72 (s, 3H), 1.68 (s, 3H), 1.67 (s, 3H), 1.65 (s, 3H), 1.60 (s, 3H), 1.34 (t, J=7.0 Hz, 6H), 1.34 (t, J=6.8 Hz, 6H); $^{13}$C NMR (100 MHz, CDCl$_3$) δ 136.8, 136.5, 131.4, 124.4, 121.2, 117.9 (t, J$_{CP}$=8.1 Hz), 80.8 (t, J$_{CP}$=150.6 Hz), 63.4 (t, J$_{CP}$=3.2 Hz), 63.4 (t, J$_{CP}$=4.5 Hz, 2C), 63.0 (t, J$_{CP}$=3.6 Hz, 2C), 40.1, 30.2, 26.7, 25.8, 25.8, 18.2, 17.7, 16.6 (t, J$_{CP}$=2.4 Hz, 2C), 16.6 (t, J$_{CP}$=3.0 Hz, 2C), 16.5; $^{31}$P NMR (121 MHz, CDCl$_3$) δ 19.1.

Bisphosphonate 4d.

Yield, 29%; colorless oil; $^1$H NMR (500 MHz, CDCl$_3$) δ 5.45 (t, J=6.5 Hz, 1H), 5.31 (tt, J=6.9 HZ, J$_{HP}$=1.4 Hz, 1H), 4.33 (d, J=6.7 Hz, 2H), 4.28-4.18 (m, 8H), 2.87 (td, J$_{HP}$=14.7 Hz, J=6.8 Hz, 2H), 1.73 (s, 6H), 1.67 (s, 3H), 1.65 (s, 3H), 1.34 (t, J=7.6 Hz, 6H), 1.34 (t, J=7.2 Hz, 6H); $^{13}$C NMR (125 MHz, CDCl$_3$) δ 136.6, 133.3, 121.2, 118.1 (t, J$_{CP}$=7.8 Hz), 80.8 (t, J$_{CP}$=150.5 Hz), 63.5 (t, J$_{CP}$=5.2 Hz), 63.3 (t, J$_{CP}$=3.2 Hz, 2C), 63.1 (t, J$_{CP}$=3.7 Hz, 2C), 30.4, 26.1, 25.8, 18.2, 18.1, 16.6 (t, J$_{CP}$=2.6 Hz, 4C); $^{31}$P NMR (201 MHz, CDCl$_3$) δ 19.0; HRMS (ES$^+$, m/z) calcd for (M+Na)$^+$ C$_{19}$H$_{38}$O$_7$NaP$_2$: 463.1991. found: 463.1989.

Phosphonic Acid 5b.

Yield, 12%; white solid; $^1$H NMR (500 MHz, D$_2$O) δ 5.65 (t, J=6.5 Hz, 1H), 5.39 (t, J=6.2 Hz, 1H), 5.27-5.18 (m, 2H), 4.32 (d, J=6.9 Hz, 2H), 2.88 (td, J$_{HP}$=14.1 Hz, J=6.5 Hz, 2H), 2.19-2.12 (m, 4H), 2.11-2.05 (m, 4H), 1.70 (s, 6H), 1.69 (s, 6H), 1.65 (s, 3H); $^{13}$C NMR (125 MHz, D$_2$O) δ 141.2, 137.1, 133.7, 133.5, 125.2, 124.7, 121.3, 119.7 (t, J$_{CP}$=7.8 Hz), 79.5 (t, J$_{CP}$=131.8 Hz), 62.7 (t, J$_{CP}$=6.5 Hz), 39.4, 38.9, 28.7, 26.1, 25.7, 25.0, 18.5, 17.1, 17.1, 15.9, 15.6; $^{31}$P NMR (201 MHz, D$_2$O) 17.5. HRMS (ES$^-$, m/z) calcd for (M−H)$^-$ C$_{21}$H$_{37}$O$_7$P$_2$: 463.2015. found: 463.2021.

Phosphonic Acid 5c.

Yield, 17%; white solid; $^1$H NMR (500 MHz, D$_2$O) δ 5.65 (t, J=6.3 Hz, 1H), 5.39 (t, J=6.6 Hz, 1H), 5.25 (t, J=6.0 Hz, 1H), 4.31 (d, J=7.0 Hz, 2H), 2.87 (td, J$_{HP}$=13.3 Hz, J=6.4 Hz, 2H), 2.20-2.12 (m, 2H), 2.11-2.05 (m, 2H), 1.75 (s, 3H), 1.70 (s, 6H), 1.69 (s, 3H), 1.65 (s, 3H); $^{13}$C NMR (125 MHz, D$_2$O) δ 138.7, 137.1, 133.6, 124.7, 121.1, 119.7 (t, J$_{CP}$=7.8 Hz), 79.5 (t, J$_{CP}$=131.7 Hz), 62.7 (t, J$_{CP}$=6.0 Hz), 39.3, 28.9, 26.0, 25.0, 24.9, 17.5, 17.1, 15.5; $^{31}$P NMR (201 MHz, D$_2$O) δ 17.5. HRMS (ES$^-$, m/z) calcd for (M−H)$^-$ C$_{16}$H$_{29}$O$_7$P$_2$: 395.1389; found: 395.1400.

Bisphosphonate Salt 5d.

Yield, 87%; white solid; $^1$H NMR (500 MHz, D$_2$O) δ 5.70 (s, 1H), 5.39 (t, J=5.9 HZ, 1H), 4.30 (d, J=6.7 Hz, 2H), 2.82 (td, J$_{HP}$=12.4 Hz, J=5.7 Hz, 2H), 1.75 (s, 3H) 1.74 (s, 3H), 1.69 (s, 3H), 1.68 (s, 3H); $^{13}$C NMR (125 MHz, D$_2$O) δ 137.9, 132.7, 121.7, 121.5 (t, J$_{CP}$=7.7 Hz), 80.4 (t, J$_{CP}$=127.1 Hz), 62.4 (t, J$_{CP}$=5.5 Hz), 30.3, 25.3, 25.1, 17.5, 17.4; $^{31}$P NMR (201 MHz, D$_2$O) δ 17.7;

Phosphonic Acid 6a.

Yield, 73%; white solid; $^1$H NMR (300 MHz, D$_2$O) δ 5.38 (t, J=6.7 Hz, 1H), 4.25 (t, J=7.2 Hz, 2H), 3.67 (t, J$_{HP}$=16.2 Hz, 1H), 1.74 (s, 3H), 1.68 (s, 3H); $^{13}$C NMR (100 MHz, D$_2$O) δ 140.2, 119.9, 74.1 (t, J$_{CP}$=140.6 Hz), 69.8, 25.1, 17.5; $^{31}$P NMR (121 MHz, D$_2$O) δ 13.9. HRMS (ES$^-$, m/z) calcd for (M−H)$^-$ C$_6$H$_{21}$3O$_7$P$_2$: 259.0137. found: 259.0145.

Phosphonic Acid 6b.

Yield, 17%; white solid; $^1$H NMR (300 MHz, D$_2$O) δ 5.49 (t, J=6.6 Hz, 1H), 5.29-5.21 (m, 1H), 4.32 (d, J=7.1 Hz, 2H), 3.67 (t, J$_{HP}$=15.2 Hz, 1H), 2.25-2.08 (m, 4H), 1.74 (s, 3H), 1.72 (s,3H), 1.66 (s, 3H); $^{13}$C NMR (75 MHz, D$_2$O) δ 142.1, 133.8, 124.3, 120.8, 75.7 (t, J$_{CP}$=130.3 Hz), 69.8, 39.0, 25.8, 24.9, 17.0, 15.8; $^{31}$P NMR (121 MHz, D$_2$O) δ 14.1;

Ether 7.

Yield, 23%; colorless oil; $^1$H NMR (500 MHz, CDCl$_3$) δ 5.10-5.05 (m, 1H), 4.20-4.12 (m, 8H), 3.75 (dd, J$_{HP}$=8.7 Hz, J=1.9 Hz, 2H), 3.63-3.57 (m, 2H), 2.05-1.89 (m, 2H), 1.70-1.53 (m, 2H), 1.66 (s, 3H) 1.59 (s, 3H), 1.43-1.28 (m, 2H), 1.34 (t, J=7.4 Hz, 6H), 1.23-1.12 (m, 1H), 0.90 (d, J=6.7 Hz,3H); $^{13}$C NMR (125 MHz, CDCl$_3$) δ 130.1, 124.0, 71.2 (d, J$_{CP}$=11.5 Hz), 64.3 (d, J$_{CP}$=165.6 Hz), 61.4 (d, J$_{CP}$=5.7 Hz, 2C), 36.4, 35.7, 28.6, 24.9, 24.7, 18.7, 16.8, 15.7 (d, J$_{CP}$=5.4 Hz, 2C); $^{31}$P NMR (201 MHz, CDCl$_3$) δ 21.0; HRMS (ES$^+$, m/z) calcd for (M+H)$^+$ C$_{15}$H$_{32}$O$_4$P$_2$: 307.2038; found: 307.2044.

Monoalkylated Bisphosphonate 8.

Yield, 53%; colorless oil; $^1$H NMR (400 MHz, CDCl$_3$) δ 5.12-5.05 (m, 1H), 4.30-4.20 (m, 8H), 3.91 (t, J=17.6 Hz, 1H), 3.85-3.75 (m, 2H), 2.06-1.88 (m, 2H), 1.73-1.49 (m, 2H), 1.67 (s, 3H), 1.60 (s, 3H), 1.47-1.25 (m, 2H), 1.36 (t, J=7.0 Hz, 12H), 1.23-1.12 (m, 1H), 0.91 (d, J=6.7 Hz, 3H); $^{13}$C NMR (100 MHz, CDCl$_3$) 130.5, 124.3, 73.2 (t, J$_{CP}$=157.0 Hz), 73.0 (t, J$_{CP}$=4.6 Hz), 62.9 (t, J$_{CP}$=3.1 Hz), 62.8 (t, J$_{CP}$=3.3 Hz), 62.7 (t, J$_{CP}$=3.5 Hz), 62.7 (t, J$_{CP}$=3.2 Hz), 36.7, 36.4, 28.8, 25.2, 25.0, 19.0, 17.2, 16.1 (t, J$_{CP}$=3.6 Hz, 2C), 16.0 (t, J$_{CP}$=3.1 Hz, 2C); $^{31}$P NMR (121 MHz, CDCl$_3$) δ 15.8; HRMS (ES$^+$, m/z) calcd for (M+H)$^+$ C$_{19}$H$_{41}$O$_7$P$_2$: 443.2328; found: 443.2325.

Dialkylated Ether 9.

Yield, 45%; colorless oil; $^1$H NMR (400 MHz, CDCl$_3$) δ 5.46 (t, J=6.3 Hz, 1H), 5.15-5.05 (m, 2H), 4.29-4.16 (m, 8H), 3.87-3.78 (m, 2H), 2.79 (td, J$_{HP}$=14.8 Hz, J=6.6 Hz, 2H), 2.14-1.90 (m, 6H), 1.76-1.52 (m, 4H), 1.68 (s, 3H), 1.65 (s, 3H), 1.60 (s, 3H), 1.60 (s, 3H), 1.40-1.30 (m, 15H), 1.22-1.12 (m, 1H), 0.89 (d, J=6.5 Hz, 3H); $^{13}$C NMR (100 MHz, CDCl$_3$) δ 136.8, 131.3, 131.1, 124.9, 124.4, 117.8 (t, J$_{CP}$=7.9 Hz), 81.0 (t, J$_{CP}$=150.4 Hz), 84.7 (t, J$_{CP}$=5.5 Hz), 63.3 (t, J$_{CP}$=2.9 Hz), 63.3 (t, J$_{CP}$=3.6 Hz), 62.9 (t, J$_{CP}$=3.2 Hz), 62.9 (t, J$_{CP}$=4.3 Hz), 40.0, 37.4 (2C), 29.9, 29.4, 26.7, 25.7 (2C), 25.5, 19.6, 17.7, 17.6, 16.6 (t, J$_{CP}$=3.3 Hz, 2C), 16.5 (t, J$_{CP}$=3.3 Hz, 2C), 16.4; $^{31}$P NMR (121 MHz, CDCl$_3$) δ 19.2; HRMS (ES$^+$, m/z) calcd for (M+H)$^+$ C$_{29}$H$_{57}$O$_7$P$_2$: 579.3580; found: 579.3573.

Bisphosphonate Salt 10.

Yield, 17%; white solid; $^1$H NMR (500 MHz, D$_2$O) δ 5.73 (t, J=5.5 Hz, 1H), 5.28-5.22 (m, 2H), 3.85-3.73 (m, 2H), 2.87-2.75 (m, 2H), 2.20-1.95 (m, 6H), 1.71 (s, 3H), 1.70 (s, 3H), 1.67 (s, 3H), 1.65 (s, 3H), 1.64 (s, 3H), 1.61-1.45 (m, 2H), 1.44-1.31 (m, 2H), 1.22-1.12 (m, 1H), 0.89 (d, J=6.4H, 3H); $^{13}$C NMR (125 MHz, D$_2$O) δ 136.0, 133.5, 133.1, 125.5, 124.9, 121.6, 80.0 (t, J$_{CP}$=126.5 Hz), 64.9, 39.5, 37.3, 36.9, 29.4, 26.2, 25.0 (3C), 24.9, 19.2, 17.1, 17.0, 15.5; $^{31}$P NMR (201 MHz, D$_2$O) δ 17.7;

Bisphosphonate 11.

Compound 3 (521 mg, 1.18 mmol) was added into a solution of NaH (66 mg, 1.65 mmol) in anhydrous DMF (20 mL) and the reaction mixture was allowed to stir for 30 minutes. After 4-fluorobenzyl bromide (0.30 mL, 2.00 mmol) was added and the reaction was allowed to stir at room temperature overnight. Saturated ammonium chloride (NH$_4$Cl) was added to quench the reaction on the following day. The resulting residue was then extracted with EtOAc and washed with brine. The remaining organic layer was dried (MgSO$_4$) and concentrated in vacuo, and the residue was purified by automated column chromatography (0-5% EtOH in Hexane) to afford compound 11 as a colorless oil (329 mg, 51%): $^1$H NMR (300 MHz, CDCl$_3$) δ 7.38-7.33 (m, 2H), 6.63 (t, J=8.4 Hz, 2H), 5.38 (t, J=6.6 Hz, 1H), 5.13 (t, J=6.0 Hz, 1H), 4.55 (d, J=6.6 Hz, 2H), 3.34 (t, J=12.5 Hz, 2H), 2.14-2.04 (m, 4H), 1.71 (s, 3H), 1.69 (s, 3H), 1.64 (s, 3H), 1.29 (t, J=7.2 Hz, 6H), 1.23 (t, J=7.2 Hz, 6H); $^{31}$P NMR (121 MHz, CDCl$_3$) δ 18.4; $^{19}$F NMR (282 MHz, CDCl$_3$) δ −117 (m)

Bisphosphonic Acid 12.

The base, 2, 4, 6-collidine (0.80 mL, 5.74 mmol) was added to the ice cold solution of bisphosphonate 11 (315 mg, 0.57 mmol) in CH$_2$Cl$_2$ (10 mL) followed by the addition of excess TMSBr (0.80 mL, 5.74 mmol). The reaction was slowly allowed to warm to room temperature and allowed to stir overnight. Once the reaction was complete the following day, the solvent was removed under vacuo. The resulting residue was further washed with toluene and concentrated repeatedly to remove any remaining TMSBr. It was then treated with NaOH solution (2.30 mL 1M NaOH & 3 mL H$_2$O) for 30 minutes and then the water was removed under vacuo to obtain the crude salt. This material was precipitated with dry acetone to obtain the desired product 12, as a white solid (193 mg, 64%): $^1$H-NMR (300 MHz, D$_2$O) δ 7.40-7.35 (m, 2H), 6.94 (t, J=8.9 Hz, 2H), 5.31 (t, J=6.6 Hz, 1H), 5.15 (t, J=6.6 Hz, 1H), 4.38 (d, J=6.6 Hz, 2H), 3.27 (t, J=12.7 Hz, 2H), 2.11-2.00 (m, 4H), 1.64 (s, 3H), 1.61 (s, 3H), 1.58 (s, 3H); $^{31}$P NMR (121 MHz, D$_2$O) δ 16.4; $^{19}$F NMR (282 MHz, D$_2$O) 8-118.

Bisphosphonate 13.

Compound 3 (1008 mg, 2.29 mmol) was added into a solution of NaH (130 mg, 3.20 mmol) in anhydrous DMF (30 mL) and the reaction mixture was allowed to stir for 30 minutes. 3-Bromobenzyl bromide (975 mg, 3.89 mmol) was then added and the reaction was allowed to stir at room temperature overnight. Saturated ammonium chloride (NH$_4$Cl) was added to quench the reaction on the following day. The resulting residue was then extracted with EtOAc and washed with brine. The remaining organic layer was dried (MgSO$_4$) and concentrated in vacuo, and the residue was purified by automated column chromatography (0-5% EtOH in Hexane) to afford compound 13 as a colorless oil (453 mg, 33%).

Bisphosphonic Acid 14.

The base, 2, 4, 6-collidine (1.00 mL, 7.38 mmol), was added into the ice cold solution of bisphosphonate 13 (450 mg, 0.74 mmol) in CH$_2$Cl$_2$ (15 mL) followed with the addition of excess TMSBr (1.00 mL, 7.38 mmol). The reaction was allowed to warm slowly to room temperature and allowed to stir overnight. Once the reaction was complete the following day, the solution was removed under vacuo. The resulting residue was further washed with toluene and concentrated repeatedly to remove any remaining TMSBr. It was then treated with NaOH solution (2.95 mL 1M NaOH & 3 mL H$_2$O) for 30 minutes and then the water was removed in vacuo to obtain the crude salt. This material was precipitated with dry acetone to obtain the desired product 14, as a white solid (306 mg, 71%): $^1$H NMR (300 MHz, D$_2$O) δ 7.64 (s, 1H), 7.25 (d, J=7.2 Hz, 1H), 7.34 (d, J=8.0 Hz, 1H), 7.14 (t, J=7.5 Hz, 1H), 5.30 (t, J=6.6 Hz, 1H), 5.17 (t, J=6.5 Hz, 1H), 4.38 (d, J=6.6 Hz, 2H), 3.25 (t, J=12.2 Hz, 2H), 2.15-2.00 (m, 4H), 1.65 (s, 3H), 1.62 (s, 3H), 1.59 (s, 3H); $^{31}$P NMR (121 MHz, D$_2$O) δ 16.1.

The following compounds may be synthesized using methods analogous to those described herein and known in the art, using appropriate starting materials and reagents. The compounds are shown as sodium salts; the freebase [—PO$_3$H$_2$] of and the ethyl ester [—PO$_3$(Et)$_2$] of each compound can also be made by methods known in the art and are hereby disclosed and included as compounds of the invention.

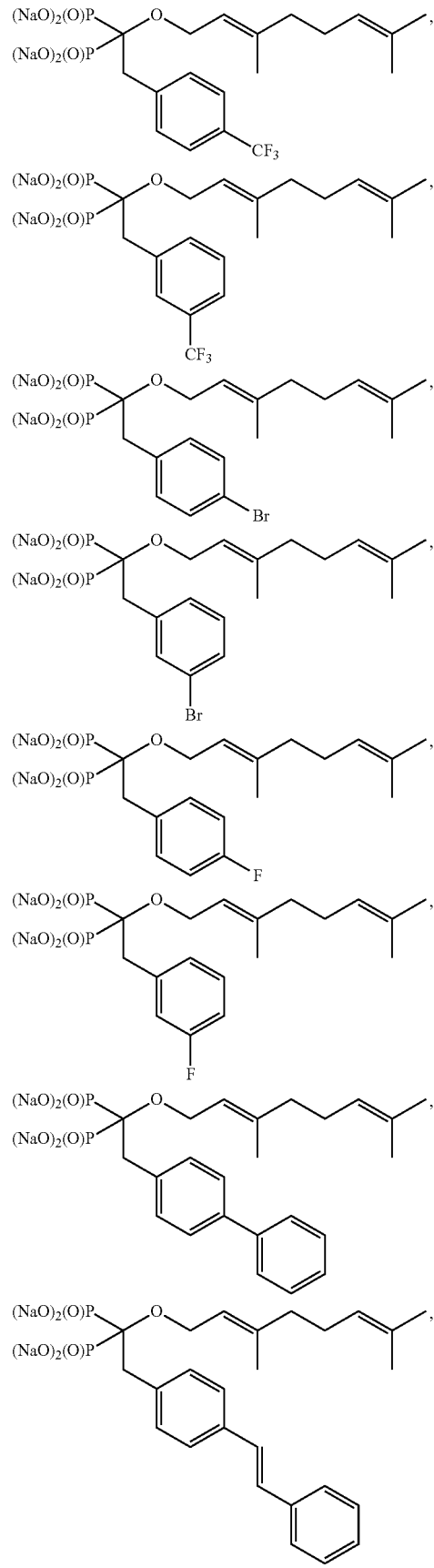

-continued
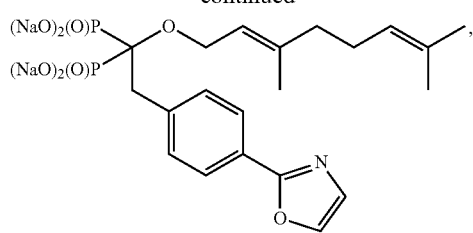
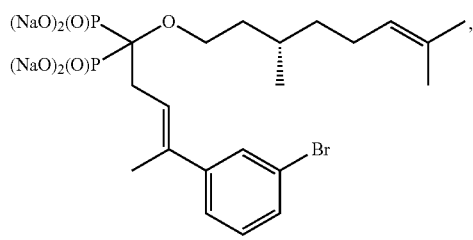
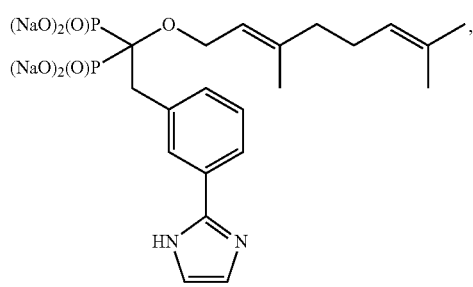
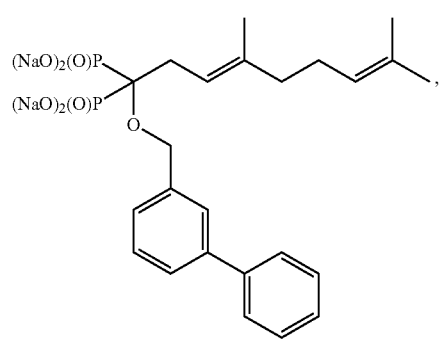
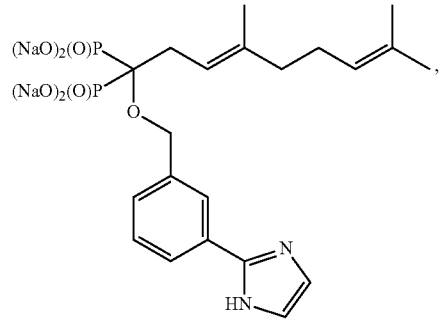
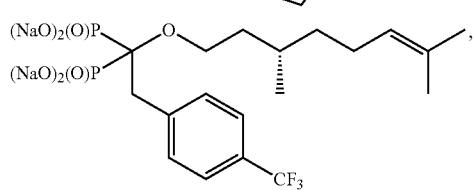
-continued
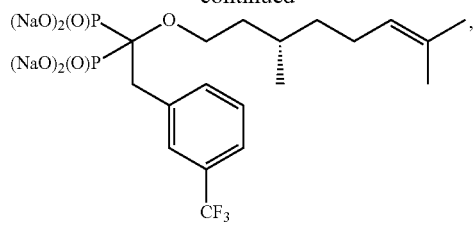
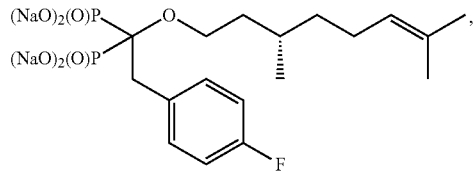
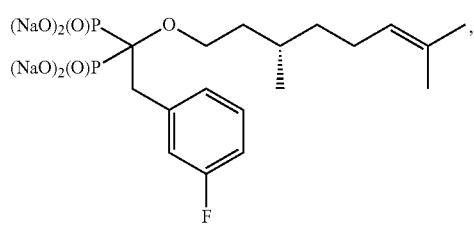
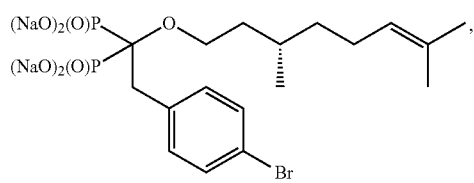
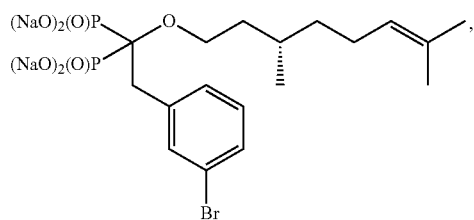
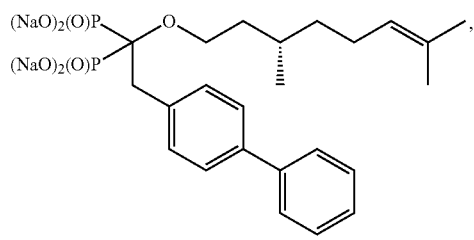
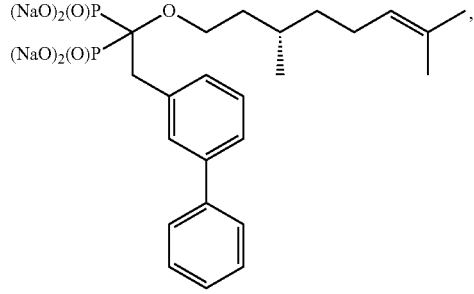

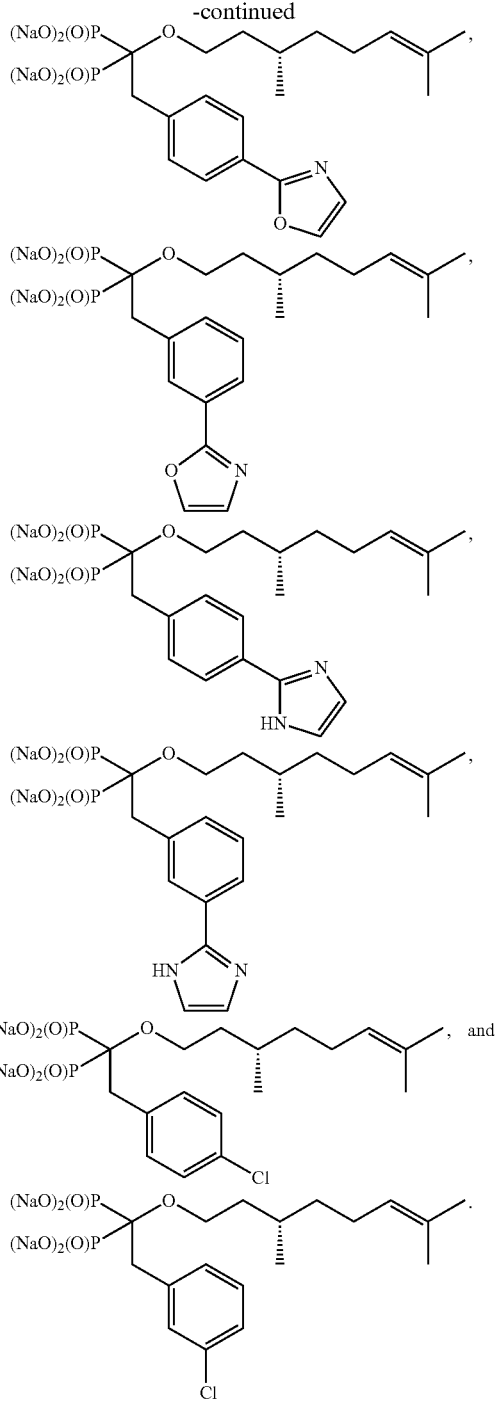

Example 2

The following illustrate representative pharmaceutical dosage forms, containing a compound of formula I or formula II ('Compound X'), for therapeutic and/or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents cited herein are incorporated by reference herein, as though individually incorporated by reference. The invention has been described with reference to various specific and pre-

What is claimed is:

1. A compound of formula I:

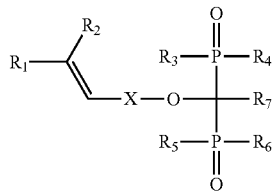

wherein:
X is —(CH$_2$)$_m$— or —(CH$_2$)$_m$CH(CH$_3$)—
m is an integer from 1 to 2;
R$_1$ is a saturated or unsaturated (C$_1$-C$_{20}$)alkyl chain;
R$_2$ is H or methyl;
each R$_3$, R$_4$, R$_5$, and R$_6$ is independently OH, or (C$_1$-C$_6$) alkoxy;
R$_7$ is

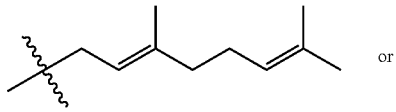 or

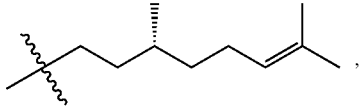, or a salt thereof.

2. A pharmaceutical composition comprising a compound as described in claim 1 and a pharmaceutically acceptable carrier.

3. The compound of claim 1 which is:

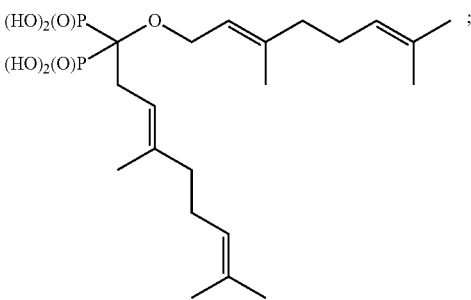

or a salt thereof.

4. A pharmaceutical composition comprising a compound as described in claim 3 and a pharmaceutically acceptable carrier.

* * * * *